(12) United States Patent
Lee et al.

(10) Patent No.: US 8,877,446 B2
(45) Date of Patent: Nov. 4, 2014

(54) METHOD FOR DETECTING PROTEIN-PROTEIN INTERACTIONS IN CELLS

(75) Inventors: Seung Goo Lee, Daejeon (KR); Su-Lim Choi, Daejeon (KR); Jong Sik Gam, Daejeon (KR); Jae Jun Song, Daejeon (KR); Sang Jun Lee, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/524,868

(22) Filed: Jun. 15, 2012

(65) Prior Publication Data

US 2013/0052660 A1    Feb. 28, 2013

(30) Foreign Application Priority Data

Aug. 26, 2011 (KR) .................. 10-2011-0086057
Jun. 14, 2012 (KR) .................. 10-2012-0063804

(51) Int. Cl.
*C12Q 1/68* (2006.01)
*G01N 33/542* (2006.01)
*G01N 33/50* (2006.01)
*G01N 21/64* (2006.01)

(52) U.S. Cl.
CPC .......... *G01N 21/6428* (2013.01); *G01N 33/542* (2013.01); *G01N 33/5008* (2013.01)
USPC ........................................ 435/6.19; 436/172

(58) Field of Classification Search
None
See application file for complete search history.

(56) References Cited

U.S. PATENT DOCUMENTS

| | | | |
|---|---|---|---|
| 6,153,398 A * | 11/2000 | Collart et al. ................... 435/26 |
| 2002/0009752 A1 * | 1/2002 | Burke et al. ................... 435/7.1 |
| 2003/0077252 A1 * | 4/2003 | Solomon et al. ............. 424/93.2 |
| 2004/0219584 A1 * | 11/2004 | Xu et al. ........................... 435/6 |
| 2008/0020438 A1 * | 1/2008 | Matsuda et al. .............. 435/167 |
| 2008/0153111 A1 * | 6/2008 | Nibert et al. ................... 435/7.8 |
| 2010/0021951 A1 * | 1/2010 | Matsumoto .................... 435/24 |
| 2010/0285451 A1 * | 11/2010 | Blau et al. ......................... 435/6 |

OTHER PUBLICATIONS

Perrin (2003) MCB 23:119-130.*
Edwards et al., "An in vivo imaging-based assay for detecting protein interactions over a wide range of binding affinities," Analytical Biochemistry 395:166-177, 2009.
BioBricks Foundation, "SB5.0 the Fifth International Meeting on Synthetic Biology," SB5.01 2011, Jun. 15-17, 2011, Stanford, CA, sb5.biobriocks.org.

* cited by examiner

*Primary Examiner* — Chris L Chin
*Assistant Examiner* — R. Moerschell
(74) *Attorney, Agent, or Firm* — Seed IP Law Group PLLC

(57) ABSTRACT

The present invention relates to a method for detecting protein-protein interactions in living cells, and more particularly, to a method for providing cells comprising a first construct and a second construct, wherein the first construct comprises a polynucleotide encoding a first fusion protein which comprises a bait protein, a first fluorescent protein and a CBD (cellulose-binding domain) protein, and wherein the second construct comprises a polynucleotide encoding a second fusion protein which comprises a prey protein and a second fluorescent protein so as to allow formation of inclusion bodies, and detecting interactions between the bait protein and the prey protein that are displayed by inclusion bodies, a method for isolating the prey protein bound to the bait protein using the cells comprising the constructs, the cells, and a kit for detecting protein-protein interactions, comprising the constructs.

17 Claims, 13 Drawing Sheets

US 8,877,446 B2

METHOD FOR DETECTING PROTEIN-PROTEIN INTERACTIONS IN CELLS

CROSS-REFERENCE TO RELATED APPLICATIONS

This application claims the benefit of Korean Patent Application Nos. 10-2011-0086057, filed Aug. 26, 2011, and 10-2012-0063804, filed Jun. 14, 2012.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 550077_402_SEQUENCE_LISTING_.txt. The text file is 9 KB, was created on Jun. 15, 2012, and is being submitted electronically via EFS-Web.

BACKGROUND OF THE INVENTION

1. Field of the Invention

The present invention relates to a method for detecting protein-protein interactions in living cells, and more particularly, to a method for providing cells comprising a first construct and a second construct, wherein the first construct comprises a polynucleotide encoding a first fusion protein which comprises a bait protein, a first fluorescent protein and a CBD (cellulose-binding domain) protein, and wherein the second construct comprises a polynucleotide encoding a second fusion protein which comprises a prey protein and a second fluorescent protein so as to allow formation of inclusion bodies, and detecting interactions between the bait protein and the prey protein that are displayed by inclusion bodies, a method for isolating the prey protein bound to the bait protein using the cells comprising the constructs, the prepared cells, and a kit for detecting protein-protein interactions comprising the constructs.

2. Description of the Related Art

Many functions of organisms are regulated by a network of intermolecular interactions. Thus, understanding of protein-protein interactions (PPI) in cells is an important issue in current biological research. PPI has been mainly examined by in vitro experiments such as immunoprecipitation and tandem affinity purification (TAP). However, there are limitations to the in-vitro approach for the analysis of dynamic protein-protein interactions in-vivo. In addition, an yeast two-hybrid (Y2H) system has been used for highly sensitive detection of PPIs under in vivo conditions. However, a Y2H system is disadvantageous in that it must be performed in yeast, nuclear translocation is required, and it relies on the indirect readout of secondary induced transcriptional activation and effects, not in direct contact, resulting in false-positives.

In order to overcome the above disadvantages, numerous methods have been developed, based on fluorescence techniques such as FRET (fluorescence resonance energy transfer), fluorescence complementation assay, and fluorescence co-localization. Among them, FRET is a method of detecting changes in fluorescence spectrum when a donor protein and an acceptor protein are within a distance of 2-8 nm, in which direct excitation of the donor molecule results in resonance energy transfer to the acceptor molecule, provided two fluorescent molecules at different wavelength are adjacent to each other. Fluorescence complementation assay is a technique of visualizing protein-protein interactions in living cells, based on fluorescence recovery due to complementation of GFP fragments, in which a fluorescent protein is split into N- and C-terminal fragments, the fragment is attached to each binding protein and expressed in the cell, and fusion of the two proteins results in reconstitution of N- and C-terminal fragments of the fluorescent protein that could be visualized. Even though the two methods are useful for the analysis of protein interactions in animal cells using a high speed sorter flow cytometry, the methods are difficult to apply for bacterial cells. For example, the detection level of FRET is too low to detect weak signals from bacterial cells considerably smaller than eukaryotic cells. Fluorescence complementation assay may show non-uniform protein expression in cells of a large size, and is influenced by other factors in bacterial cells, leading to false-positive results.

Fluorescence co-localization is used by localization in particular organelles of eukaryotic cells, but cannot be applied to a bacterial system that has no cell organelles. A recent study reported that a fluorescent PPI complex formed by co-expression of a bait protein-fused cell division protein and a fluorescent prey protein is recruited to the cell pole of *E. coli* (Edwards, A. N., et al., 2009. An in vivo imaging-based assay for detecting protein interactions over a wide range of binding affinities. Anal. Biochem. 395:166-77.).

The present inventors have made many efforts to develop a method for analyzing interactions between biomolecules in living cells. As a result, they found that *Cellulomonas fimi*-derived family II cellulose-binding domain (CBD) is self-aggregated to form inclusion bodies (IB) in *E. coli*, and CBD-induced IB has a feature of capturing a particular interacting protein in the particles when the interacting proteins are co-expressed. Accordingly, the present inventors intended to develop a new fluorescence co-localization method by using the inclusion bodies as artificial cell organelles in bacterial cells as well as eukaryotic cells. Finally, the present inventors found that an antiparallel leucine zipper is used as a model of interacting proteins to observe fluorescence co-localization to inclusion bodies (FCIB) using a fluorescence microscope and a high speed sorter flow cytometer so that interactions between the proteins having low binding affinity can be analyzed and isolated, thereby completing the present invention.

SUMMARY OF THE INVENTION

An object of the present invention is to provide a method for detecting protein-protein interactions in cells, comprising the steps of (i) providing cells comprising a first construct and a second construct, wherein the first construct comprises a polynucleotide encoding a first fusion protein which comprises a bait protein, a first fluorescent protein and a CBD (cellulose-binding domain) protein, and wherein the second construct comprises a polynucleotide encoding a second fusion protein which comprises a prey protein and a second fluorescent protein; (ii) expressing the fusion proteins and allowing formation of inclusion bodies in the cells; and (iii) measuring fluorescence signals of the fluorescent proteins.

Another object of the present invention is to provide a method for isolating a prey protein interacting with a bait protein, comprising the steps of (i) providing cells comprising a first construct and a second construct, wherein the first construct comprises a polynucleotide encoding a first fusion protein which comprises a bait protein, a first fluorescent protein and a CBD (cellulose-binding domain) protein, and wherein the second construct comprises a polynucleotide encoding a second fusion protein which comprises a prey protein and a second fluorescent protein; (ii) expressing the fusion proteins and allowing formation of inclusion bodies in the cells; and (iii) isolating the prey protein bound to the bait protein.

Still another object of the present invention is to provide cells introduced with the constructs.

Still another object of the present invention is to provide a kit for detecting protein-protein interactions comprising the constructs.

DETAILED DESCRIPTION OF THE PREFERRED EMBODIMENTS

Figure 1:
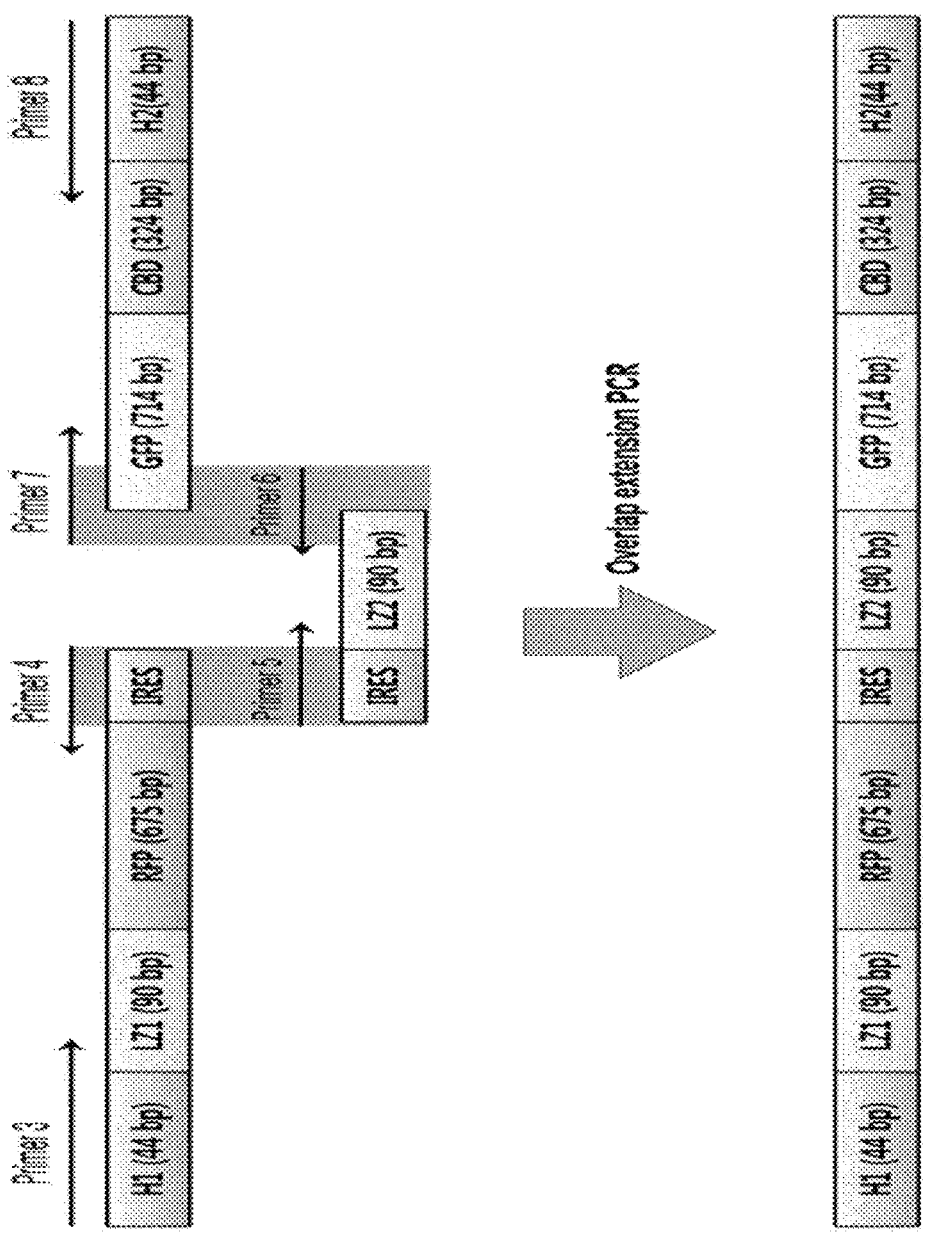
FIG. 1 is a schematic diagram showing the structure of a leucine zipper-fused CBD (LZ1-RFP and LZ2-GFP-CBD) by overlap PCR,wherein "H1" and "H2" refer to homologous DNA sequences located in cloning sites of vector pET21a to be used for recombination cloning and are non-coding sequences.

In one aspect to achieve the above objects, the present invention provides a method for detecting protein-protein interactions in cells, comprising the steps of (i) providing cells comprising a first construct and a second construct, wherein the first construct comprises a polynucleotide encoding a first fusion protein which comprises a bait protein, a first fluorescent protein and a CBD (cellulose-binding domain) protein, and wherein the second construct comprises a polynucleotide encoding a second fusion protein which comprises a prey protein and a second fluorescent protein; (ii) expressing the fusion proteins and allowing formation of inclusion bodies in the cells; and (iii) measuring fluorescence signals of the fluorescent proteins.

The method of the present invention is developed to improve the disadvantages of the conventional methods of detecting protein-protein interactions, such as FRET (fluorescence resonance energy transfer), fluorescence complementation, and fluorescence co-localization. In the method of the present invention, the CBD protein tags form the inclusion bodies in cells, and the fluorescent proteins are localized into the inclusion bodies, and therefore, protein-protein interactions can be easily detected. The known inclusion bodies are inactive, and thus have a limit in the detection of interactions between active proteins. However, the CBD protein of the present invention exposes many hydrophobic residues, and thus the binding proteins form inclusion bodies under normal protein-folding conditions. Therefore, it has an advantage of detecting actual interactions between active proteins in vivo. In addition, this advantage eliminates concern of protein expression level to avoid a reduction of interaction signals by overexpression. That is, this method has an advantage of removing noise due to overexpression.

As used herein, the term "bait protein" is a protein used to detect a protein that interacts therewith, and it is displayed by inclusion bodies to bind with a prey protein interacting therewith, and recruits fluorescence into the inclusion bodies that act as artificial organelles in cells. As used herein, the term "prey protein" means a protein that is able to interact with the bait protein. The bait protein and the prey protein are, but not limited to, substances to be interacted therewith, such as a variety of therapeutic proteins and signal transduction proteins. The bait protein and the prey protein may be functional domains and parts of polypeptides, as well as native proteins. For detection or screening of interactions, the bait protein is a known material used by the experimenter, and the prey protein is an unknown material, but is not limited thereto.

Preferably, the polynucleotides encoding the bait protein and the prey protein may be those derived from libraries including genes encoding various proteins, which may be obtained from the entire genome of an organism, such as entire genomic DNA and cDNA libraries. In addition, the polynucleotide encoding the bait protein and the prey protein may be obtained from any subset of the entire genome, e.g., a subtracted library or a sized library.

As used herein, the terms "first fluorescent protein" and "second fluorescent protein" mean substances capable of producing signals that can be detected by those skilled in the art, and examples thereof may be a fluorescent protein selected from the group consisting of GFP (Green Fluorescent Protein), EGFP (Enhanced Green Fluorescent Protein), mGFP (modified green fluorescent protein), RFP (Red Fluorescent Protein), mRFP (Monomeric Red Fluorescent Protein), ERFP (Enhanced Red Fluorescent Protein), DsRed (*Discosoma* sp. red fluorescent protein), BFP (Blue Fluorescent Protein), EBFP (Enhanced Blue Fluorescent Protein), CFP (Cyan Fluorescent Protein), CGFP (Cyan Green Fluorescent Protein), ECFP (Enhanced Cyan Fluorescent Protein), YFP (Yellow Fluorescent Protein), EYFP (Enhanced Yellow Fluorescent Protein), AzG (Azami Green), HcR (HcRed, *Heteractis crispa* red fluorescent protein) and BFP (Blue Fluorescent Protein), but are not limited thereto.

The first fluorescent protein and the second fluorescent protein may be identical fluorescent proteins, but preferably the first fluorescent protein and the second fluorescent protein may be different fluorescent proteins that emit different fluorescence colors for convenient distinction. According to one embodiment of the present invention, GFP was used as the first fluorescent protein in the bait protein, and RFP was used as the second fluorescent protein in the prey protein. Therefore, they emit different fluorescence colors to easily detect interactions when the bait protein and the prey protein are co-expressed.

In the step of (i) providing cells comprising a first construct and a second construct, wherein the first construct comprises a polynucleotide encoding a first fusion protein which comprises a bait protein, a first fluorescent protein and a CBD (cellulose-binding domain) protein, and wherein the second construct comprises a polynucleotide encoding a second fusion protein which comprises a prey protein and a second fluorescent protein, the first and second constructs may exist within individual vectors or within a single vector.

If they exist within individual vectors, the vector comprising the polynucleotide encoding the first fusion protein which comprises the bait protein, the first fluorescent protein and the CBD (cellulose-binding domain) protein may be a vector capable of expressing a protein prepared by fusion of the first fluorescent protein and the bait protein at the N-terminus of CBD fusion protein, and the vector comprising the polynucleotide encoding the second fusion protein which comprises the prey protein and the second fluorescent protein may be a vector capable of expressing a fusion protein prepared by fusion of the prey protein at the N-terminus of the second fluorescent protein.

Figure 2:
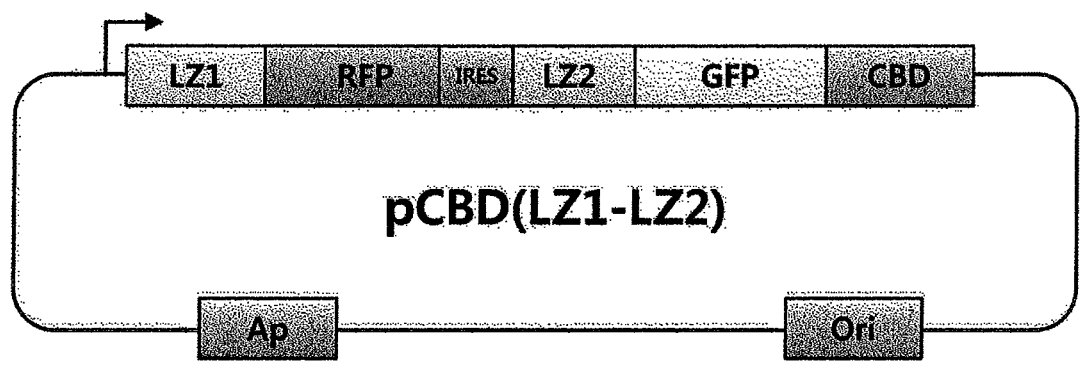
FIG. 2 is a schematic diagram showing the genetic map of pCBD(LZ1-LZ2) and pCBD(LZ1)
Figure 2:
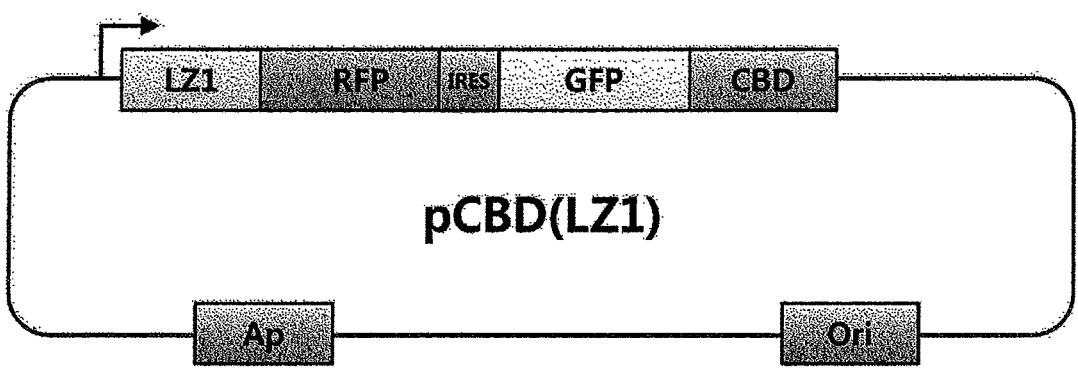
Figure 4:
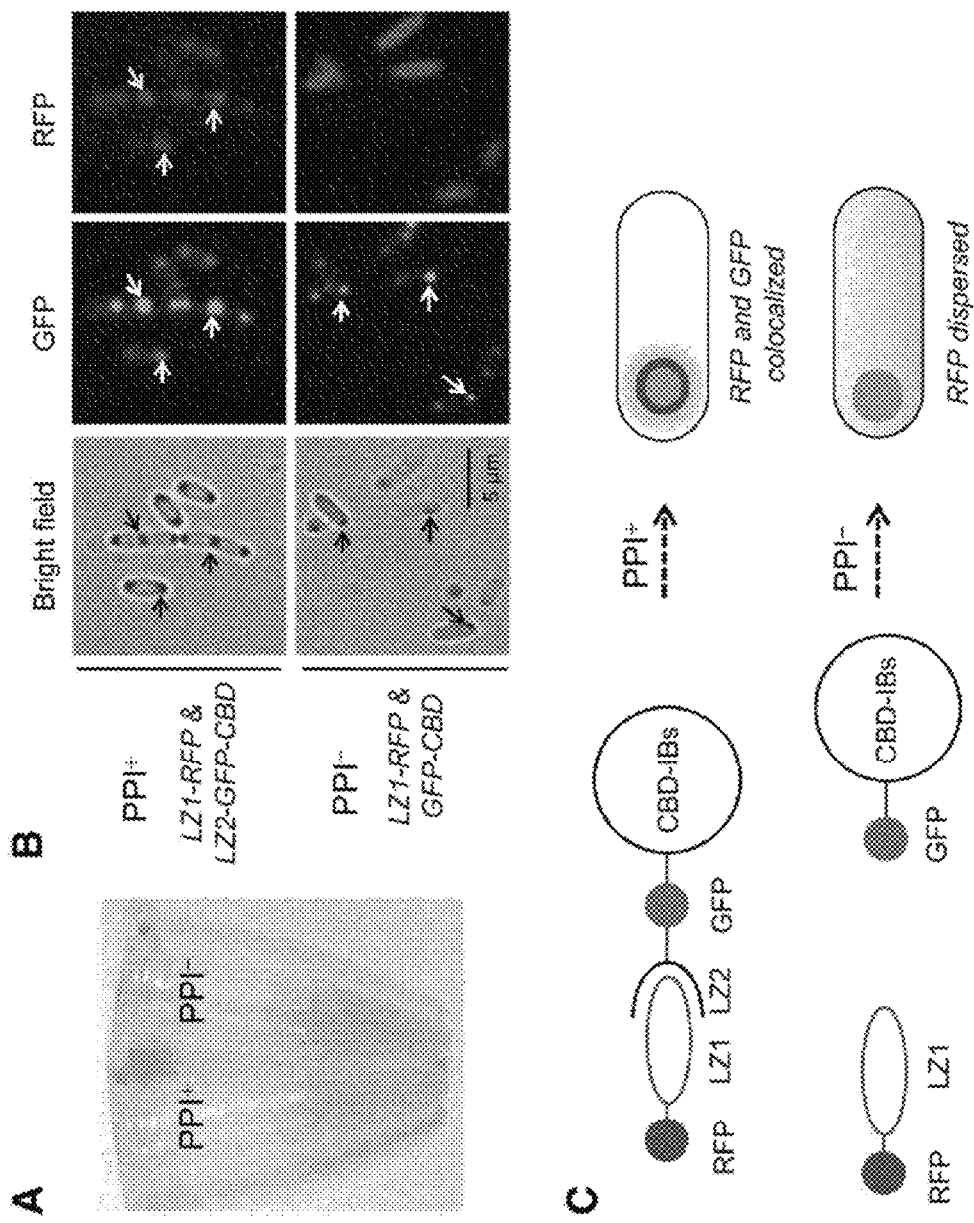
FIG. 4 shows the microscopic results of protein-protein interactions (PPI) between leucine zippers (LZ1 and LZ2) using FCIB (fluorescence co-localization to inclusion bodies), in which (A) is the result of visual observation of the culture broth of cells including PPI$^+$ (left; colorless) or PPI$^-$ (right; red) at 6 hours after expression of bait and prey proteins, (B) is the result of microscopic observation of cells including PPI$^+$ (LZ1-RFP and LZ2-GFP-CBD protein) or PPI$^-$ (LZ1-RFP and GFP-CBD protein), and (C) shows the relationship between PPIs and co-localization of fluorescent inclusion bodies, wherein PPI$^+$ shows RFP and GFP co-localization in inclusion bodies, and PPI$^-$ shows dispersed RFP proteins instead of formation of GFP foci.
Figure 5:
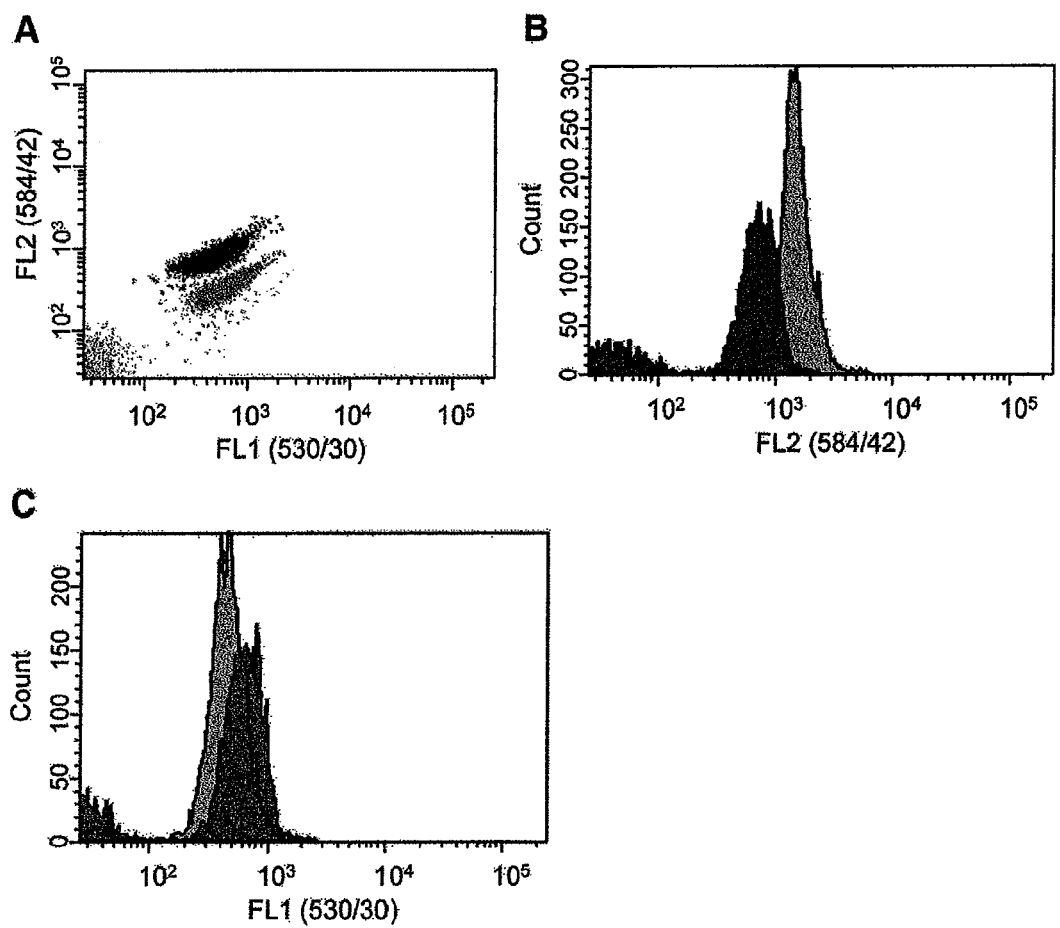
FIG. 5 shows the flow cytometric results of PPIs between LZ1 and LZ2 leucine zippers in FCIB, in which (A) shows fluorescence analysis of PPI$^+$ cells (light gray dot) or PPI$^-$ cells (black dot) on FL1 and FL2 plot, (B) shows a comparison between PPI$^+$ (deep gray) cells and PPI$^-$ (light gray) cells in FL2 (RFP) histogram, and (C) shows a comparison of PPI$^+$ (deep gray) cells and PPI$^-$ (light gray) cells in FL1 (GFP) histogram.
Figure 8:
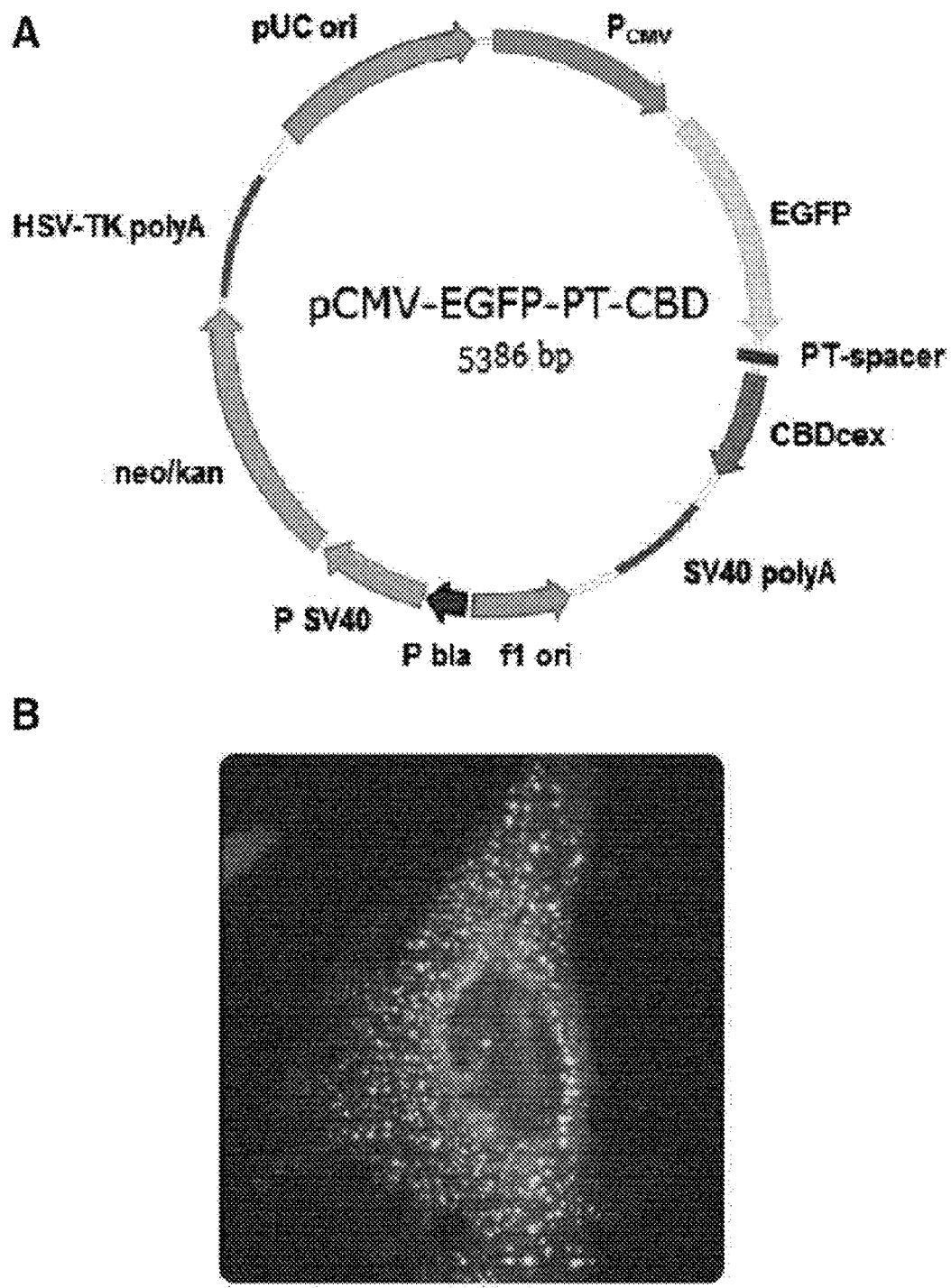
FIG. 8 show the result of formation of GFP inclusion bodies by CBD fusion in animal cells (HeLa), in which (A) shows a vector prepared by cloning the GFP-CBD gene into an E. coli-animal cell shuttle vector (pCMV), and (B) is the result of microscopic observation of inclusion bodies of GFP-CBD expressed in animal cells.

If they exist within a single vector, the vector may be a vector where the first construct comprising the polynucleotide encoding the first fusion protein which comprises the bait protein, the first fluorescent protein and the CBD (cellulose-binding domain) protein, and the second construct comprising the polynucleotide encoding the second fusion protein which comprises the prey protein and the second fluorescent protein are linked to each other by a nucleic acid including IRES (internal ribosome entry site) sequence. Preferably, the IRES sequence may be a nucleic acid sequence of SEQ ID NO. 11. According to one embodiment of the present invention, leucine zipper 2 (LZ2) was used as the bait protein, GFP was used as the first fluorescent protein, leucine zipper 1 (LZ1) was used as the prey protein, and RFP was used as the second fluorescent protein to prepare a pCBD(LZ1-LZ2) vector, which was used to co-express the "LZ1-RFP" fusion protein and the "LZ2-GFP-CBD" fusion protein in cells, and then LZ1 and LZ2 interactions were observed (FIGS. 4 and 5). The schematic diagram of the structure of the vector is shown in FIG. 2. Expression in animal cells can be performed by a shuttle vector as shown in FIG. 8. In addition, according to one embodiment of the present invention, the interactions between the bait protein and the prey protein were quantitatively analyzed using leucine zippers having different binding affinities (Example 13 and 14).

Further, the first construct or the second construct may further include any polynucleotide such as an expression control sequence, but is not limited thereto.

As used herein, the term "operably linked" means the association of one polynucleotide fragment with the other polynucleotide fragment so that the function or expression thereof is affected by the other, but available combinations of the polynucleotide fragments cause no detectable effect when each fragment performs its function. For instance, the term refers to a functional linkage between a polynucleotide coding for a target protein and an expression control sequence in such a manner as to allow general functions. Further, the polynucleotide encoding the fluorescent protein may be linked to the polynucleotide encoding the bait protein, the prey protein and/or the CBD protein in a manner which allows for the function or expression of the fluorescent protein, but is not limited thereto. The operable linkage may be prepared using a genetic recombinant technique that is well known in the art, and site-specific DNA cleavage and ligation may be carried out using enzymes that are generally known in the art.

As used herein, the term "vector" refers to an expression vector capable of expressing a target protein in suitable host cells, and to a gene construct that includes essential regulatory elements to which a gene insert is operably linked in such a manner as to be expressed. The vector of the present invention may include a signal sequence or a leader sequence for targeting membranes or secretion as well as expression regulatory elements, such as a promoter, an operator, an initiation codon, a stop codon, a polyadenylation signal and an enhancer, and can be constructed in various forms depending on the purpose thereof. The promoter of the vector may be constitutive or inducible. In addition, expression vectors include a selectable marker that allows the selection of host cells containing the vector, and replicable expression vectors include a replication origin. The vector may be self-393 replicable, or may be integrated into the DNA of a host cell. The vector includes a plasmid vector, a cosmid vector, a viral vector or the like.

In the present invention, the step of providing cells including the first construct and the second construct may be performed by introduction of a single vector or individual vectors into suitable cells.

As used herein, the term "introduction" means insertion of foreign DNA into a cell by transformation or transduction. The transformation may be performed by various methods known in the art, such as a CaCl$_2$ precipitation, a Hanahan method that is an improved CaCl$_2$ method by using DMSO (dimethyl sulfoxide) as a reducing material, electroporation, calcium phosphate precipitation, protoplast fusion, agitation using silicon carbide fiber, *Agrobacterium*-mediated transformation, PEG-, dextran sulfate-, lipofectamine-, and desiccation/inhibition-mediated transformation. The term "transduction" means the delivery of a gene to a cell using a virus or viral vector particle by means of infection.

As used herein, the term "CBD (cellulose-binding domain) protein" refers to a protein that allows the formation of inclusion bodies in cells, and may be used as a fusion tag to facilitate formation of inclusion bodies in cells. The CBD protein may be fused at C-terminus of the bait protein or the fluorescent protein, but is not limited thereto. Any protein can be used as the CBD protein without limitation, as long as it is able to induce formation of inclusion body. For example, *Cellulomonas fimi*-derived family II CBD can be used as the CBD protein, but is not limited thereto. The CBD protein of the present invention includes the protein having an amino acid sequence of SEQ ID NO. 28, but is not limited thereto. Also the polynucleotide encoding the CBD protein is derived from the CBD region of *Cellulomonas-fimi* exoglucanase (cex) gene (GenBank: M15824.1) having a polynucleotide of SEQ ID NO. 29, but is not limited thereto. In one embodiment of the present invention, it was found that *Cellulomonas fimi*-derived family II CBD was self-aggregated in *E. coli* to form inclusion bodies (inclusion bodies, IB) (Example 8).

The inclusion bodies act as artificial cell organelles in cells to localize the fusion proteins in the inclusion bodies.

The method for detecting protein-protein interactions in cells may further include the step of (iv) determining that the bait protein and the prey protein are interacted when fluorescence is localized in the inclusion bodies. When the bait protein and the prey protein are not interacted, the first fluorescent protein linked to the bait protein only exists on the inclusion bodies formed by CBD, and the second fluorescent protein fused to the prey protein is dispersed in the cytosol. When the bait protein and the prey protein are interacted, the bait protein binds to the prey protein, which is brought into the inclusion bodies formed by CBD, resulting in localization of the first and second fluorescent proteins in the inclusion bodies. The fluorescence signal localized in the inclusion bodies may be indicative of the interaction of the bait protein and the prey protein. The principle of the present invention is shown in FIG. 4C.

In addition, the method for detecting protein-protein interaction in cells may be a method of the quantitative analysis of the interaction of the bait protein and the prey protein. As the interaction of the bait protein and the prey protein is increased, the fluorescence intensity of the second fluorescent protein linked to the prey protein is decreased and the fluorescence intensity of the first fluorescent protein linked to the bait protein is increased.

Figure 12:
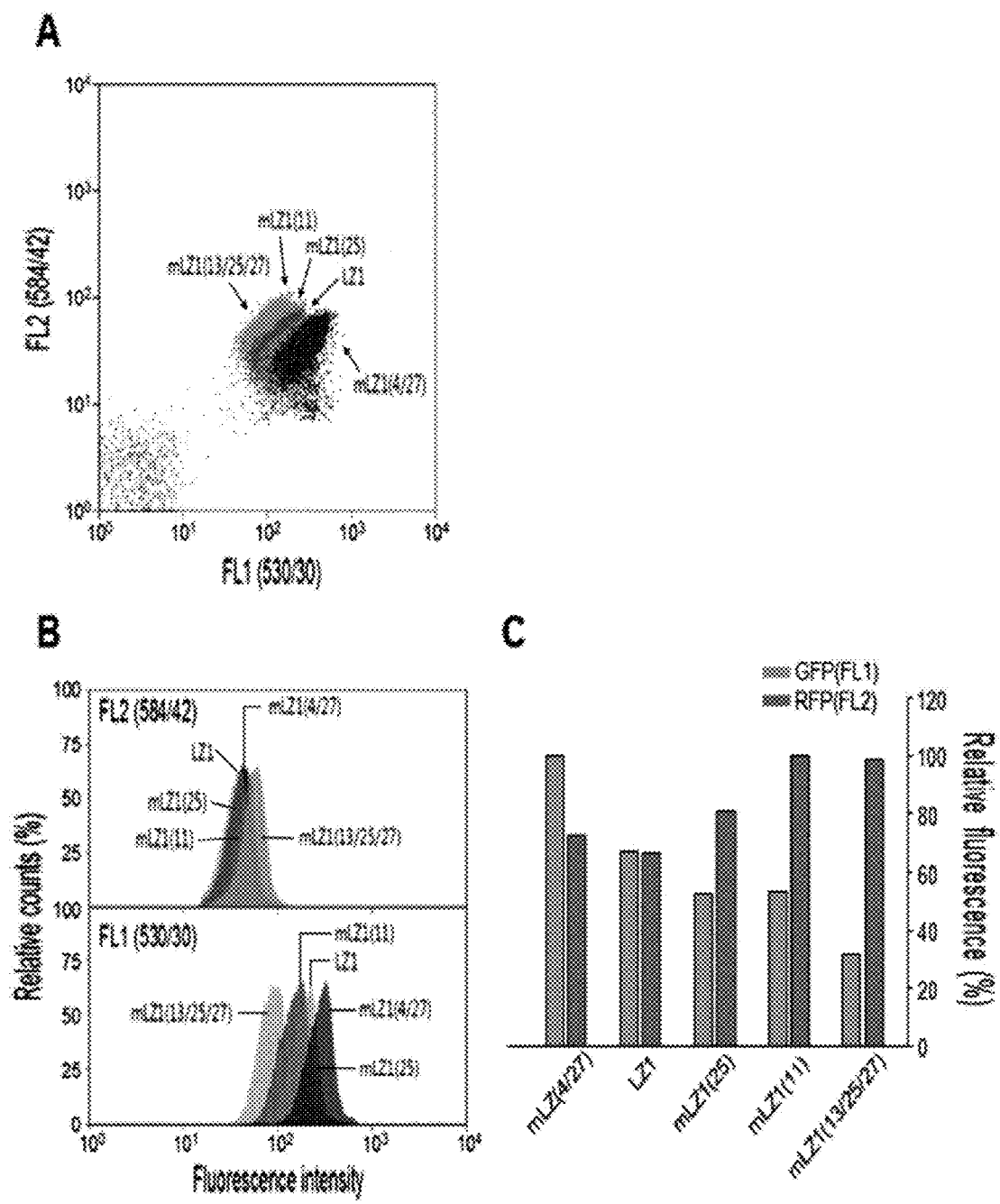
FIG. 12 is the flow cytometric results of binding affinity between mLZ1 and LZ2 in mutant cells, in which (A) shows fluorescence distribution of each strain according to binding affinity in FL1 and FL2 plot, (B) shows fluorescence changes of RFP or GFP in FL2 or FL1 histogram and (C) shows relative mean fluorescence values of GFP(FL1) and RFP (FL2)
Figure 13:
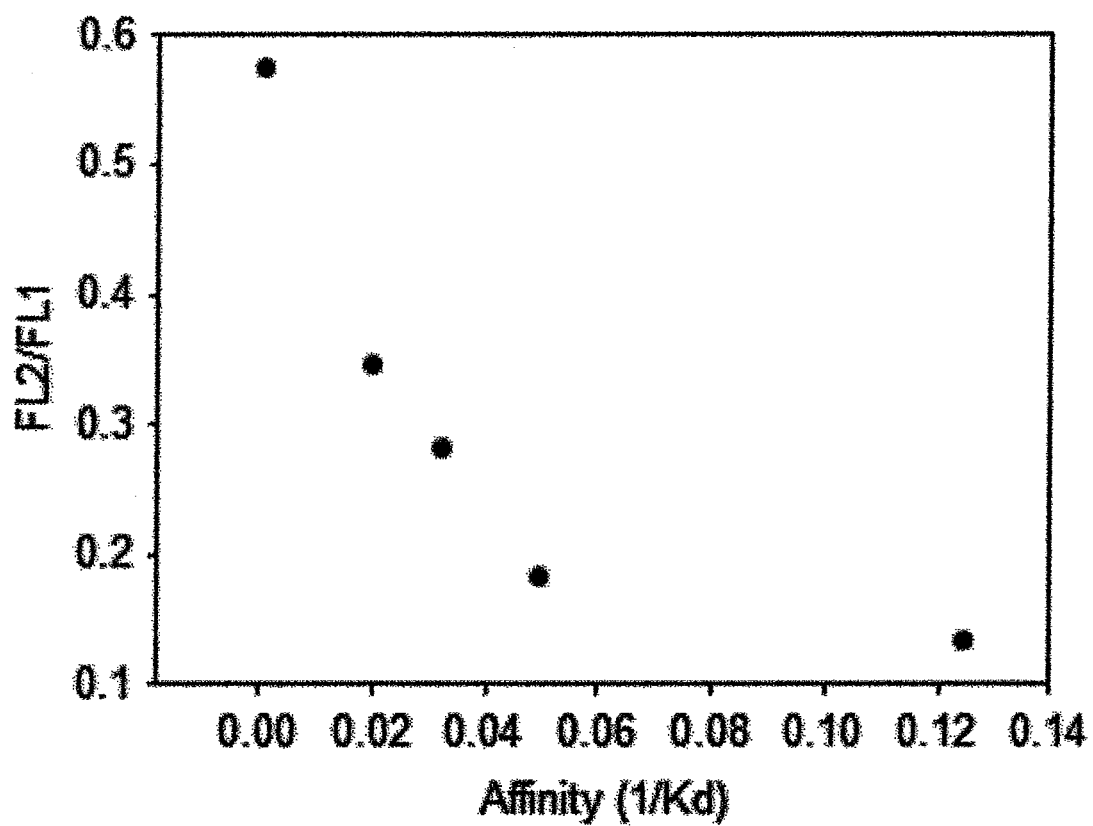
FIG. 13 shows the pattern of FCIB values (FL2/FL1 ratio) according to binding affinity, when fluorescence of mLZ1-LZ2 was measured by flow cytometry.

Hence, the interaction of the bait protein and the prey protein can be quantitatively analyzed by the ratio of the fluorescence intensity of the second fluorescent protein to the fluorescence intensity of the first fluorescent protein. In one embodiment of the present invention, the interaction of the bait protein and the prey protein were quantitatively analyzed using LZ1 mutants having different binding affinities and it was confirmed that a ratio of RFP to GFP (FL2/FL1 ratio) depends on affinity (FIGS. 12 and 13).

The fluorescence detection may be performed using a fluorescence detector, and preferably a fluorescence microscope or flow cytometry.

Figure 10:
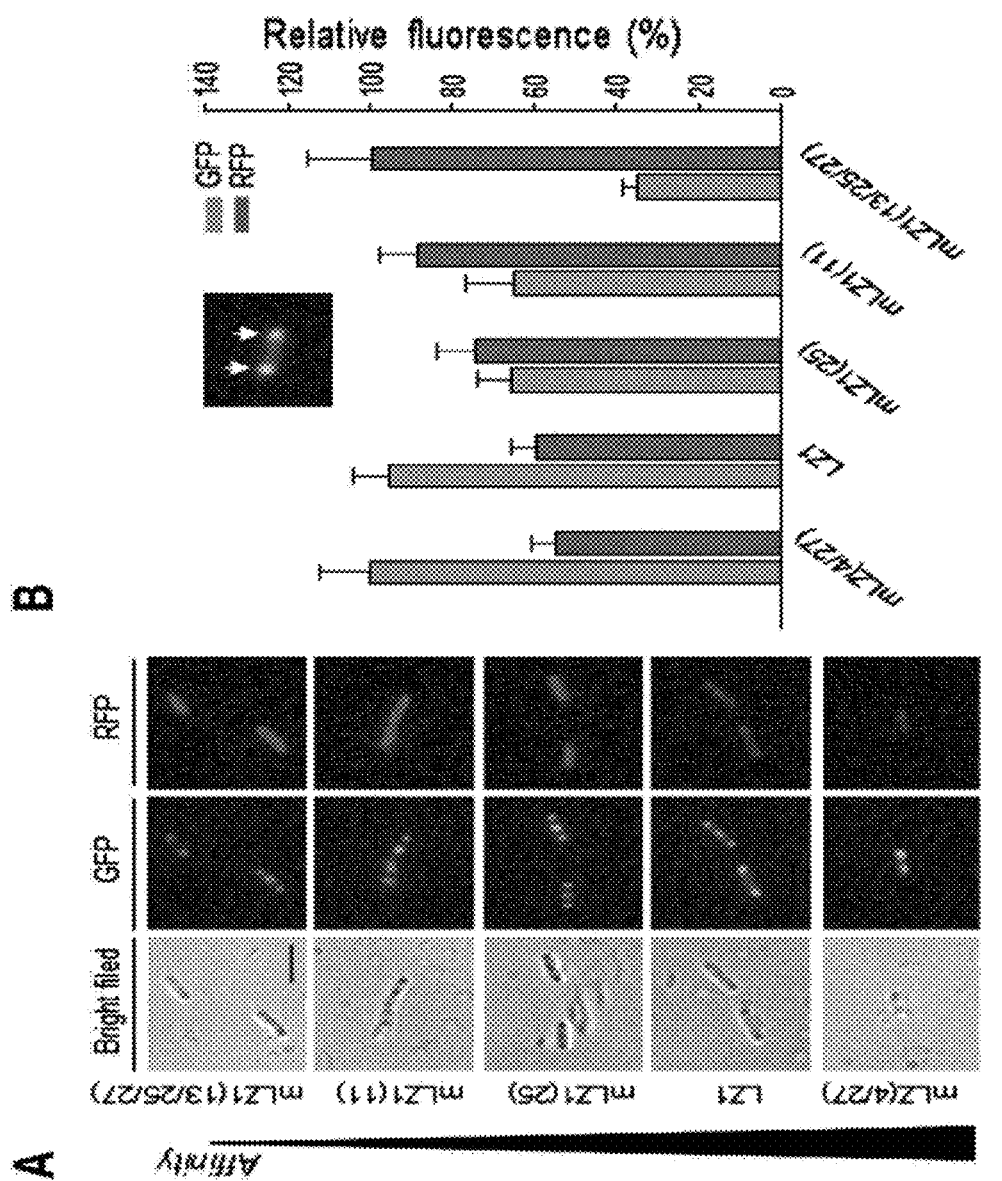
FIG. 10 is fluorescence microscopic images showing localization of RFP protein into GFP inclusion bodies according to binding affinity between mLZ1 and LZ2 in mutant strains, in which (A) shows that localization in cells occurs according to binding affinity, and (B) shows changes in GFP and RFP fluorescence in inclusion bodies according to binding affinity.

In order to examine whether interactions between the bait protein and the prey protein in living cells can be detected by the method of the present invention, the present inventors found that when the inclusion bodies are formed by CBD at the C-terminus of the fluorescent protein, non-CBD-fused GFP proteins are dispersed in the cytosol whereas CBD-fused GFP proteins are highly observed in the inclusion bodies (FIGS. 3A to C), and there was no influence on GFP functions and thus the dispersed fluorescent proteins and the fluorescent proteins localized in the inclusion bodies were clearly distinguishable by fluorescence microscopy and flow cytometry. Moreover, antiparallel leucine zipper proteins, LZ2 and LZ1 known to interact with each other were used as the bait protein and the prey protein, respectively. The "LZ1-RFP" and "LZ2-GFP-CBD" fusion proteins were co-expressed in bacterial cells, and their interactions (PPI$^+$) were observed under a fluorescence microscope. As a result, co-localization of green and red fluorescence was observed in the inclusion bodies in the cells (FIGS. 4B to 4C). On the contrary, it was found that when LZ2 interacting with LZ1 was not linked to the "GFP-CBD" fusion protein inducing the formation of inclusion bodies and "LZ1-RFP" and "GFP-CBD" are only co-expressed in bacterial cells, red fluorescence was dispersed in the cytosol by no protein-protein interactions (PPI$^-$) (FIGS. 4B to 4C). These results indicate that the presence and absence of protein-protein interactions in cells can be rapidly detected by the method of the present invention. Histograms were also clearly distinguished in the flow cytometric results (FIGS. 5A to C). In addition, it was found that PPI$^+$ cells and PPI$^-$ cells were selectively sorted (FIG. 6) and the inclusion bodies were formed in animal cells by the CBD protein (FIG. 8B). These results support that the detecting method of the present invention can be a method for detecting protein-protein interaction in animal cells as well as bacterial cells. Also, the detection method of the present invention can be used for quantitative analysis of the interaction of the bait protein and the prey protein (FIGS. 10, 12 and 13). These results support that the method for detecting protein-protein interactions of the present invention can be performed rapidly and simply, and can be used for quantitative analysis of the interactions.

In another aspect, the present invention provides a method for isolating a prey protein interacting with a bait protein, comprising the steps of (i) providing cells comprising a first construct and a second construct, wherein the first construct comprises a polynucleotide encoding a first fusion protein which comprises a bait protein, a first fluorescent protein and a CBD (cellulose-binding domain) protein, and wherein the second construct comprises a polynucleotide encoding a second fusion protein which comprises a prey protein and a second fluorescent protein; (ii) expressing the fusion proteins and allowing formation of inclusion bodies in the cells; and (iii) isolating the prey protein bound to the bait protein.

The descriptions of the prey protein, the bait protein, the first fluorescent protein, the second fluorescent protein, the CBD, the first construct and the second construct are the same as above.

The isolation of the prey protein may be performed by various methods, and is preferably by flow cytometry. Flow cytometry can be used to sort cells under proper conditions, and the prey proteins can be isolated by setting up the conditions of sorting the prey protein bound to the bait protein.

The isolating method of the present invention has the advantage of isolating the prey protein interacting with the bait protein in living cells.

In one embodiment, the present inventors confirmed that cells can be sorted by high speed flow cytometry, based on a difference in fluorescence intensity between the presence and absence of protein-protein interactions, and examined the sorted cells by Western blotting. As a result, only a band corresponding to LZ2-GFP-CBD was observed (FIG. 6), indicating that interacting proteins can be selectively sorted by flow cytometry.

In still another aspect, the present invention provides cells comprising a first construct and a second construct, wherein the first construct comprises a polynucleotide encoding a first fusion protein which comprises a bait protein, a first fluorescent protein and a CBD (cellulose-binding domain) protein, and wherein the second construct comprises a polynucleotide encoding a second fusion protein which comprises a prey protein and a second fluorescent protein.

The first and second constructs may exist within individual vectors or within a single vector.

In still another aspect, the present invention provides a kit for detecting protein-protein interactions, comprising (a) a first construct comprising a polynucleotide encoding a first fusion protein which comprises a bait protein, a first fluorescent protein and a CBD (cellulose-binding domain) protein, and (b) a second construct comprising a polynucleotide encoding a second fusion protein which comprises a prey protein and a second fluorescent protein.

Preferably, the kit may further comprise a vector including the first construct and the second construct, and more preferably may further comprise cells introduced with the vector.

The kit of the present invention may further comprise tools and/or reagents known in the art to be used for the detection of fluorescent proteins, in addition to the cells including the first construct and the second construct. If necessary, the kit of the present invention may further comprise a tube to be used for mixing individual ingredients, a well plate, and a manual describing detailed instructions.

Experimental procedures, reagents and reaction conditions that can be used in the above-mentioned methods are conventionally known in the art and will be apparent to those skilled in the art.

Hereinafter, the present invention will be described in more detail with reference to Examples. However, these Examples are for illustrative purposes only, and the invention is not intended to be limited thereto.

Example 1

Gene and Enzyme Acquisition

Family II CBD (cellulose-binding domain) gene was cloned from the exoglucanase gene of *Cellulomonas fimi* KCTC 9143 strain deposited at the Korean Collection of Type Cultures (KCTC), at the Korea Research Institute of Bioscience and Biotechnology. The improved GFP (green fluorescent protein) gene was obtained from a commercial plasmid pEGFP (Clontech, CA). A plasmid pRFP having RFP (monomeric red fluorescent protein 1) gene was provided by KAIST (Daejeon, Korea). Two antiparallel leucine zipper genes, LZ1 (EQLEKKLQALEKKLAQLEWKNQALEK KLAQ; charged residues are underlined, SEQ ID NO. 1) and LZ2 (ALKKELQANKKELAQLKWELQALKKELAQ; charged residues are underlined, SEQ ID NO. 2) were obtained from pMRBAD-Z-CGFP and pETlla-Z-NGFP which were provided by Dr. Regan at Yale university (Magliery, T. J., et al., 2005. Detecting protein-protein interactions with a green fluorescent protein fragment reassembly trap: scope and mechanism. J. Am. Chem. Soc. 127:146-57.). All restriction enzymes were purchased from Roche Applied Science (Indianapolis, Ind.), and T4 DNA ligase was purchased from Fermentas (Glen Burnie, Md.).

Example 2

DNA Manipulation

All primers were synthesized by Bioneer in Daejeon, Korea. Primers used in the present invention are shown in the following Table 1. NdeI and XhoI restriction sites are represented in bold.

TABLE 1

| Primer name | Sequence (5'→3') | SEQ ID NO. |
|---|---|---|
| Primer 1 | GATATACATATGGTGAGCAAGGGCGAG | 3 |
| Primer 2 | GGTGCTCGAGTTACTTGTACAGCTTGTCCATGCC | 4 |
| Primer 3 | CCTCTAGAAATAATTTTGTTTAACTTTAAGAAGGAGATATACATATGGCAAGCGAGCAGCTGGAA | 5 |
| Primer 4 | CAATTCTTTTTTGAGGGCCATATGATAATCTCCTTCTTAAAGTTAAACAAAATTATTTTAGGCGCCGGTGGAGTGGCGGCC | 6 |
| Primer 5 | GGCCGCCACTCCACCGGCGCCTAAAATAATTTTGTTTAACTTTAAGAAGGAGATTATCATATGGCCCTCAAAAAGAATTG | 7 |
| Primer 6 | CAGCTCCTCGCCCTTGCTCACCTGCGCCAGTTCCTTTTTCAG | 8 |
| Primer 7 | CTGAAAAAGGAACTGGCGCAGGTGAGCAAGGGCGAGGAGCTG | 9 |
| Primer 8 | GCAGCCAACTCAGCTTCCTTTCGGGCTTTGTTAGCAGCCGGATCTCAGCCGACCGTGCAGGGCGTGCC | 10 |

The gfp gene was amplified from pEGFP using primer 1 (SEQ ID NO. 3) and primer 2 (SEQ ID NO. 4), cleaved using NdeI and XhoI, and cloned into a pET21a vector (Invitrogen, CA) to prepare pGFP. The gfp and cbd genes were fused by overlap PCR according to the method described in Ha, J.-S., et al., (2008. Thermostable beta-glycosidase-CBD fusion protein for biochemical analysis of cotton scouring efficiency. J Microbiol Biotechnol 18:443-448.), and inserted into the NdeI and HindIII sites of the pET21a vector so as to prepare a pGFP-CBD plasmid.

Two leucine zipper genes, LZ1 and LZ2 were linked to pRFP and pGFP-CBD, respectively and LZ1-RFP and LZ2-GFP-CBD fusion protein-encoding genes in the pET21 plasmid were fused by overlap PCR using primers 3 to 8 (SEQ ID NO. 5 to 10), and recombination was performed using *E. coli* DH5α cells including pKD46 according to the method described in Datsenko, K. A., et al. (2000. One-step inactivation of chromosomal genes in *Escherichia coli* K-12 using PCR products. Proc. Natl. Acad. Sci. USA 97:6640-5.). IRES (internal ribosome entry site, 5'-AATAATTTTGTT-TAACTTTAAGAAGGAGATTATCAT-3', SEQ ID NO. 11) was located between LZ1-RFP and LZ2-GFP-CBD genes (FIG. 1). The plasmid prepared by the above method was designated as pCBD (LZ1-LZ2). The pCBD(LZ1) plasmid including LZ1-RFP and GFP-CBD fusion protein-encoding gene was prepared by overlap PCR as described above (FIG. 2).

Example 3

Protein Expression

*E. coli* BL21 (DE3) was used as an expression host cell. The cells were transformed with pCBD(LZ1-LZ2) or pCBD (LZ1) prepared in Example 2, and cultured in LB media containing ampicillin (50 µg/ml). When OD at 600 nm reached 0.5, IPTG (isopropyl-1-thio-β-D-galactopyranoside, 1 mM) was added for the induction of CBD-induced inclusion bodies (CBD-IB), and the cells were incubated at 37° C. for 6 hours. Formation of inclusion bodies in the cultured cells was observed under a microscope. *E. coli* cells were disrupted by sonication on ice, and expression of the fusion protein was examined by SDS-PAGE and Western blotting. Non-aqueous fraction or CBD-IB were separated and obtained by centrifugation at 16,300×g for 10 minutes, and resuspended in PBS buffer (pH 7.4) containing Triton X-100 (0.50) to remove the membrane-bound precipitate.

Example 4

Western Blotting Analysis

The whole cell extract fraction (20 µl) was electrophoresed on SDS-PAGE (120) and transferred onto a PVF membrane (polyvinylidene fluoride membrane, Millipore, Mass.). The blot was hybridized with a primary anti-GFP mouse antibody (Sigma-Aldrich, WI), and anti-mouse-IgG goat antibody-HRP conjugate (Bio-Rad, CA) was prepared in TTBS buffer (20 mM Tris-HCl (pH 7.5), 0.1 M NaCl, 0.1% Tween-20) containing 5% skim milk. Hybridization bands were detected using Opti-4CN substrate kit (Bio-Rad, CA).

Example 5

Fluorescence Microscopy

Fluorescent *E. coli* colonies on an agar plate were observed under an AZ100 multizoom microscope (Nikon, Japan) equipped with a GFP filter (Ex: 455-485 nm, Em: 500-545 nm) and an RFP filter (Ex: 540/25 nm, Em: 605/55 nm). GFP and RFP fluorescence images of fluorescent CBD-IB-expressing *E. coli* cells were observed using an Axiovert 2000M fluorescence microscope (Carl Zeiss, Germany) equipped with a filter set 44 (Ex: BP 475/40 nm, Em: BP 530/50 nm) and a filter set 15 (Ex: BP 546/12 nm, Em: LP 590 nm). Pseudo-color images were generated by Axiovision 4.5 program (Carl Zeiss).

Example 6

Electron Microscopy

*E. coli* cells were fixed in a mixture of 2.5% paraformaldehyde and 2.5% glutaraldehyde in 0.1 M sodium phosphate buffer (pH 7.2) for 2 hours, and fixed in osmium (IV) oxide in the same buffer for 1 hour. The cells were dehydrated with ethanol and propylene oxide, and embedded in Epon-812. Ultra-thin sections were prepared using a ULTRACUTE microtome (Leica, Germany), and stained with uranyl acetate and lead citrate, followed by observation under a CM20 transmission electron microscope (Philips, Netherlands).

The isolated CBD-IB was fixed under the same conditions, dehydrated in gradient ethanol, and substituted with isoamyl acetate. Then, the samples were dried in a $CO_2$ critical point dryer, and coated with gold in a sputter coater (SC502, Polaron, UK), followed by observation under a LEO 1455VP scanning electron microscope (LEO GmbH, Germany).

Example 7

Flow Cytometry

Flow cytometry was performed using a FACS Calibur (BD Biosciences, CA). Analysis gate was set, based on SSC and FSC parameters. GFP and RFP fluorescent signals were detected by FL1 (530/30 nm) and FL2 (585/42 nm) PMT, respectively. 5,000 events were counted for each sample. Data were collected using BD CellQuest Pro (version 4.0.2, 145 BD Biosciences) software. Cell sorting was performed using a FACS Aria Cell Sorter (BD Biosciences, CA) at Korea Research Institute of Bioscience and Biotechnology, Chung-Buk. GFP and RFP fluorescent signals were detected by FITC (530/30 nm) and PE-Texas Red (610/20 nm) PMT, respectively. Data were analyzed using BD FACSDiVa software (version 4.0.2, BD Biosciences).

Example 8

Fluorescent Foci by CBD-Induced Inclusion Bodies in Bacterial Cell

Figure 3:
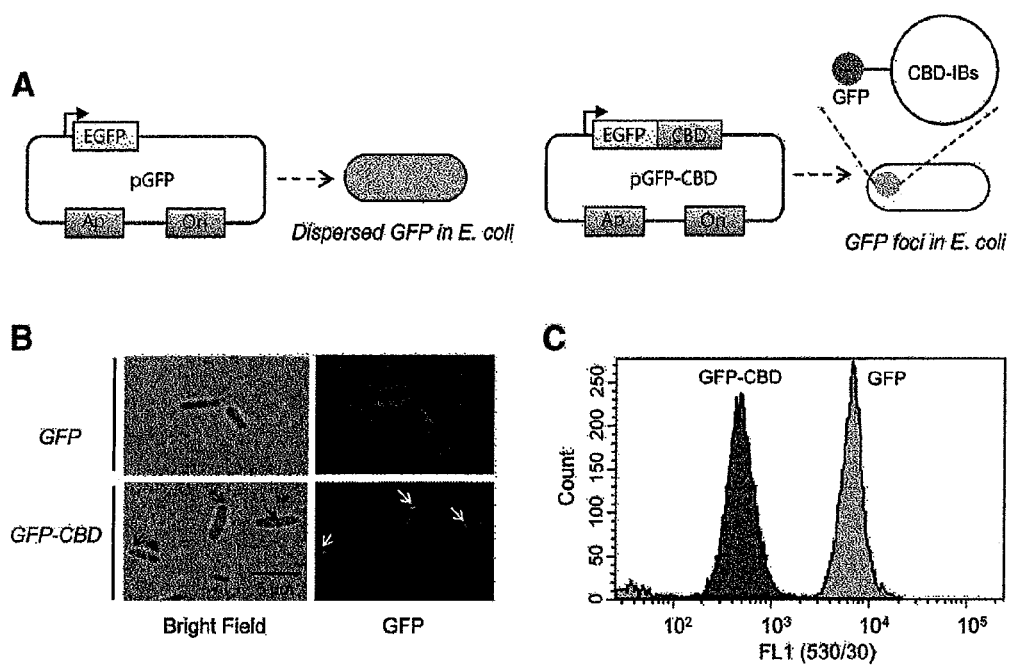
FIG. 3 is a diagram showing formation of fluorescent inclusion bodies by GFP and CBD fusion, in which (A) is a diagram showing pGFP for GFP dispersed in cytosol and pGFP-CBD for GFP foci in cells, (B) is the microscopic results of native GFP and GFP-CBD, and (C) is the flow cytometric results of cells including GFP and GFP-CBD protein, wherein light green and deep green signals represent different fluorescent distributions of two types of cells including dispersed GFP and focused GFP-CBD protein, respectively.

In order to examine the formation of fluorescent inclusion bodies (IB) by CBD fusion, IPTG-induced *E. coli* cells including pGFP or pGFP-CBD were observed (FIG. 3A).

As a result, green fluorescence was dispersed in the cytosol by single expression of gfp gene in *E. coli*, but foci of the GFP-CBD fusion protein was observed in the inclusion bodies in the cells (FIG. 3B). These results support that the CBD-induced inclusion bodies did not hinder proper folding and native form of GFP, that is, the method of the present invention is able to detect protein-protein interactions without modification of actual structures of the bait and prey proteins.

Cells having soluble GFP (light gray) in the cytosol and cells having GFP (deep gray) in the inclusion bodies were compared by flow cytometry. Consequently, the fluorescence level of the cells having GFP dispersed in the cytosol was approximately 10 times higher than that of the cells having GFP in the inclusion bodies (FIG. 3C). It is thought that this difference is attributed to high excitation of GFP dispersed in the cytosol by laser, compared to GFP on the inclusion bodies. These results support that the fluorescent proteins localized in the cell organelle inclusion bodies can be clearly distinguished from the dispersed fluorescent protein by flow cytometry as well as fluorescence microscopy.

Example 9

FCIB (Fluorescence Co-Localization to Inclusion Bodies) as Indicator of Protein Interaction It was examined whether the fluorescent inclusion bodies including the bait proteins are able to recruit the prey proteins in the cytosol. Antiparallel leucine zippers, LZ1 and LZ2 ($K_D$=20 µM) were used as a model protein forming FCIB in bacterial cells. LZ1 and LZ2 are known to form a stable heterodimer by ionic interactions between opposite charges of the peptides and interactions between hydrophobic residues, and the binding affinity is $10^5$ times higher than those of LZ1 and LZ2 homodimers.

Edward er al. ((2009) An in vivo imaging-based assay for detecting protein interactions over a wide range of binding affinities. Anal. Biochem. 395, 166-177.) reported that fluorescence image analysis using DivIVA (cell division protein) locating on a specific chromosomal region is practical and detects a wide range of binding affinity (1 nM to 15 µM). However, the FCIB technique of the present invention can be used to detect very weak PPIs such as antiparallel leucine zipper ($K_D$=20 µM), because inclusion bodies form large artificial organelles in the cells, and thus the prey protein favorably binds to the bait protein in inclusion bodies, thereby emitting stronger fluorescent signals. Therefore, it can be seen that FCIB of the present invention is a very sensitive method capable of detecting PPIs having weak binding affinity.

LZ1 was fused at the N-terminus of RFP to prepare LZ1-RFP as a prey protein, and LZ2 was linked at the N-terminus of GFP-CBD to prepare LZ2-GFP-CBD as a bait protein. Both the prey and bait proteins (LZ1-RFP and LZ2-GFP-CBD) were expressed in *E. coli* BL21(DE3) at the same time to induce PPI. Also, LZ-RFP and GFP-CBD were expressed as a control (PPI$^-$).

As a result, red fluorescence was not detected in a culture broth (PPI$^+$, FIG. 4A) whereas strong red fluorescence was surprisingly detected in a culture broth containing cells expressing both LZ1-RFP and GFP-CBD proteins (PPI$^-$, FIG. 4A).

Microscopic results showed that inclusion bodies were observed at the pole regions of both *E. coli* cells (PPI$^+$ and PPI$^-$) (black arrows in FIG. 4B), and the presence of GFP foci was clearly detected in the regions (white arrows in FIG. 4B). Microscopic observation of RFP showed that LZ1-RFPs, as indicated by yellow arrows, were also localized in the CBD-induced green fluorescent inclusion bodies showing LZ2 (FIG. 4B). However, LZ1-RFP proteins were dispersed in the cytosol, when LZ2s are not included in the green fluorescent inclusion bodies.

In conclusion, it can be seen that when PPIs occur in the cells, green and red fluorescent proteins are co-localized in the inclusion bodies in the cells. On the contrary, when PPIs do not occur in the cells, red fluorescent proteins are dispersed in the cytosol instead of co-localizing in the green fluorescent inclusion bodies (FIG. 4C). These results support that FCIB can be used to rapidly monitor PPIs in living cells.

Example 10

PPI Flow Cytometry in Bacterial Cells

Flow cytometry has been used as one of the most powerful tools in cell to cell fluorescence analysis. As mentioned above (Example 8), flow cytometric results demonstrated that GFP foci were clearly different from the GFP proteins dispersed in the cells (FIG. 3C). Thus, flow cytometry was performed to examine localization of RFP proteins in the inclusion bodies resulting from PPIs between LZ1 and LZ2, and dispersion of RFP proteins resulting from no PPIs.

As shown in FIG. 5A, PPI$^+$ cells (blue dot) and PPI$^-$ cells (black dot) on FCIB were distributed in different locations on the FL1 and FL2 plot. Data of FL1 and FL2 fluorescence intensities were divided into two histograms, individual compartments. In each histogram of RFP (FL2) and GFP (FL1), PPI$^+$ cells and PPI$^-$ cells showed clear fluorescent difference according to the presence of interactions (FIGS. 5B, 5C). As the RFP protein and GFP protein are co-localized in the inclusion bodies of PPI$^+$ cells, the fluorescence level of the RFP protein was lower than that of PPI$^-$ cells. Also the fluorescence level of the GFP protein was higher than that of PPI$^-$ cells. These results show the changes in fluorescence intensity of the fluorescent proteins in the presence and absence of the protein-protein interactions (PPI). These results support that flow cytometric results based on FCIB are very useful for PPI determination in small bacterial cells.

Figure 6:
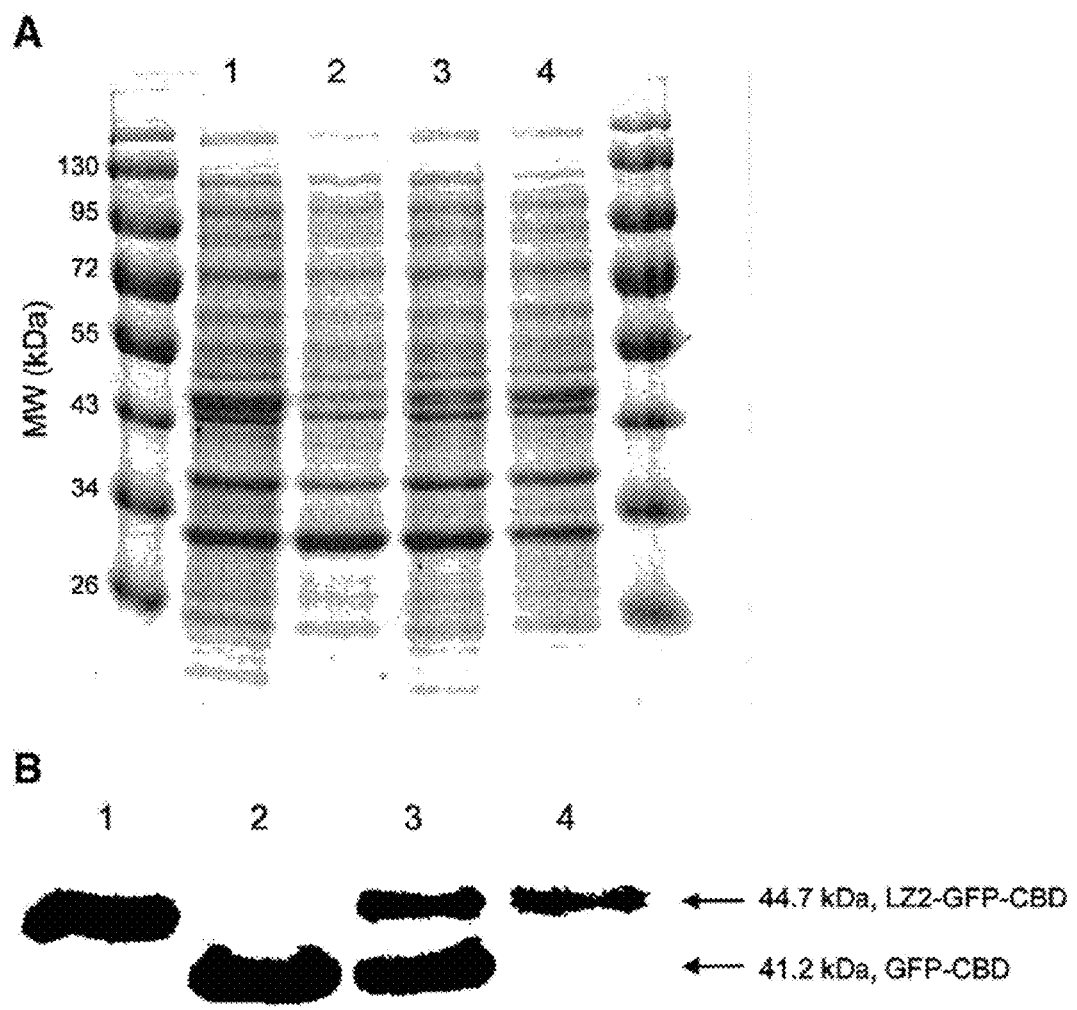
FIG. 6 shows the result of SDS-PAGE (A) and Western blotting (B) of PPI$^+$ cells sorted by FACS (fluorescence activated cell sorter), in which Lane 1 represents PPI$^+$ cells, Lane 2 represents PPI$^-$ cells, Lane 3 represents mixture of PPI$^+$ and PPI$^-$ cells, and Lane 4 represents PPI$^+$ cells sorted by FACS.

Next, the present inventors examined whether PPI$^+$ and PPI$^-$ cells can be screened by a difference in RFP fluorescence intensity using high speed flow cytometry. The PPI$^+$ and PPI$^-$ cells were mixed in equal numbers, and put into a flow cytometry. Cells were sorted from the mixture of PPI$^+$ and PPI$^-$ cells under the conditions capable of detecting PPI$^+$ cells. The sorted cells were subjected to Western blotting using anti-GFP antibody (FIG. 6).

As a result, the cells before sorting showed two mixed bands having 44.7 kDa of LZ2-GFP-CBD in PPI$^+$ cells and 41.2 kDa of GFP-CBD in PPI$^-$ cells. A strong band corresponding to LZ2-GFP-CBD was clearly observed in the lane 4 of PPI$^+$ cells sorted by Western blotting, compared to the band of GFP-CBD, supporting that bacterial cells having PPI$^+$ or PPI$^-$ can selectively be sorted using high speed analysis equipment such as FACS.

In mammalian cells, flow cytometric analysis using FRET has been used as a powerful tool for the analysis of large numbers of cells having PPIs, but FRET cells are not suitable for FACS-based screening in bacterial cells due to relatively low fluctuation. The present invention overcomes this drawback.

Example 11

Microscopy of Interacting Fluorescent Particles

Figure 7:
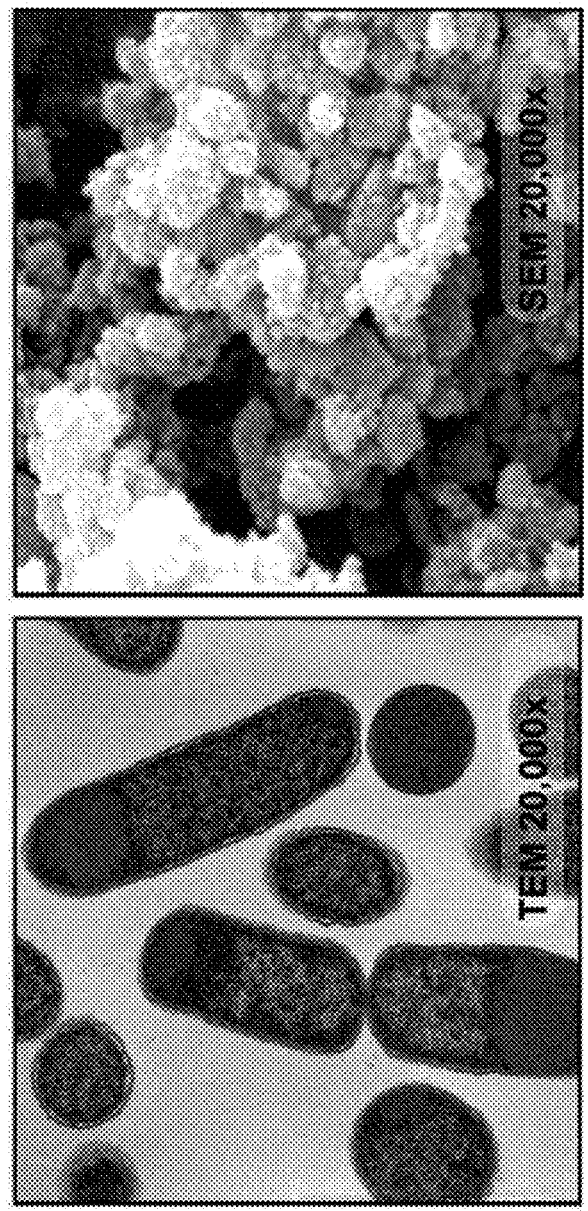
FIG. 7 shows a transmission electron microscopic image of PPI$^+$ cells expressing LZ1-RFP and LZ2-GFP-CBD protein particles (left), and a scanning electron microscopic image of isolated CBD-IB (right) (the electron microscopes are at a magnification of ×20,000)

CBD can be used as a fusion tag at the C-terminus to facilitate formation of inclusion bodies in *E. coli* cells (FIGS. 3B and 4B). Formation of in vivo inclusion bodies by CBD tag was observed under an electron microscope (FIG. 7). CBD-IB in the cells was shown as typical bent-shaped inclusion bodies in a TEM image, and the isolated inclusion bodies were shown as a multicomplex of amorphous protein particles in a SEM (scanning electron microscopy) image.

Example 12

Fluorescence Foci by CBD-Induced Inclusion Bodies in Animal Cells

It was examined whether formation of fluorescent inclusion bodies (IB) by CBD fusion is also observed in animal cells as in bacterial cells. For expression of GFP-CBD in animal cells, the GFP-CBD gene was cloned into an *E. coli*-animal cell shuttle vector, pCMV vector (Stratagene, CA) (FIG. 8A). The GFP-CBD-cloned pCMV vector was purified and recovered using a Plasmid Midi Kit (Qiagen, Germany). The HeLa (CCL-2, ATCC) was used as an animal cell line. HeLa cell line was subcultured in DMEM media (Invitrogen, CA) containing 10% serum (Fetal Bovine Serum, FBS) and 1% antibiotic-antimycotic (Invitrogen) at 37° C. in a 5% $CO_2$ incubator, and prepared for use in this experiment. The method of introduction of genes into animal cells is as follows. First, HeLa cells were cultured in a T-25 flask at 37° C. and 5% $CO_2$ until 90% confluence, and then detached from the bottom of flask by trypsin-EDTA treatment. The cells were seeded in a 4-well plate at a density of $1 \times 10^5$ cell/well, and cultured at 37° C. and 5% $CO_2$. After 24 hours, the GFP-CBD gene-cloned pCMV vector was transfected into cells using Lipofectamin™ 2000. 4 hours later, the media was replaced with DMEM media containing 10% serum, followed by cultivation at 37° C. and 5% $CO_2$ for one day. The next day, GFP-CBD-expressing HeLa cells were observed by confocal microscopy.

As a result, formation of GFP inclusion bodies by CBD induction was observed in animal cells, as in bacterial cells (FIG. 8B). These results support that CBD-induced PPI can be observed in animal cells as well as bacterial cells.

Example 13

Preparation of Leucine Zipper (LZ) Gene Having Different Binding Affinity

In Examples 9 and 10, it was confirmed that the presence of the interactions, that is, the presence of LZ2, can be detected by fluorescence microscopy and flow cytometry. Next, it was examined whether LZ1s having different binding affinities can be quantitatively detected by FCIB. Mutant mLZ1s having different binding affinities were prepared, based on the reference (Magliery, T. J., et al., 2005. Detecting protein-protein interactions with a green fluorescent protein fragment reassembly trap: scope and mechanism. J. Am. Chem. Soc. 127:146-57.).

Mutant mLZ1 (4/27) has increased binding affinity to LZ2 compared to the wild type LZ1. To the contrary, mutant mLZ1 (25), mLZ1(11) and mLZ1(13/25/27) have decreased binding affinity to LZ2 compared to LZ1. Information about amino acid sequences and binding affinities of the mLZ1 mutants (mLZ1(4/27), mLZ1(25), mLZ1(11), and mLZ1(13/25/27)) is shown in Table 2, wherein substituted amino acids are underlined.

TABLE 2

| Mutant | Amino acid sequence | Mutation locus | $K_d$ (μM) | SEQ ID NO. |
|---|---|---|---|---|
| LZ1 | EQLEKKLQALEKKLAQLEWKNQ ALEKKLAQ | none | 20 | 1 |
| mLZ1(4/27) | EQLKKKLQALEKKLAQLEWKNQ ALEKELAQ | 4/27 | 8 | 12 |
| mLZ1(25) | EQLEKKLQALEKKLAQLEWKNQ ALKKKLAQ | 25 | 31 | 13 |
| mLZ1(11) | EQLEKKLQALKKKLAQLEWKNQ ALEKKLAQ | 11 | 50 | 14 |
| mLZ1 (13/25/27) | EQLEKKLQALEKELAQLEWKNQ ALKKELAQ | 13/25/27 | 1000 | 15 |

The mutant mLZ1 genes were prepared using a Quikchange site-directed mutagenesis kit (Stratagene, CA). To prepare pCBD(mLZ1(4/27)-LZ2), primary PCR was performed using pCBD(LZ1-LZ2) as a template and primers 9 and 10 (SEQ ID NOs. 16 and 17). Secondary PCR was performed using the PCR product as a template and primers 11 and 12 (SEQ ID NOs. 18 and 19). The secondary PCR product was treated with DpnI to remove the template gene, and the pCBD(mLZ1(4/27)-LZ2) gene was transformed into the XL1-Blue competent cells. Next, to prepare pCBD(mLZ1 (25)-LZ2), PCR was performed using pCBD(LZ1-LZ2) as a template and primers 13 and 14 (SEQ ID NOs. 20 and 21), and pCBD(mLZ1(25)-LZ2)-inserted transformed strain was prepared in the same manner as above. Next, to prepare pCBD (mLZ1(11)-LZ2), PCR was performed using pCBD(LZ1-LZ2) as a template and primers 15 and 16 (SEQ ID NOs. 22 and 23), and pCBD(mLZ1(11)-LZ2)-inserted transformed strain was prepared in the same manner as above. Next, to prepare pCBD(mLZ1(13/25/27)-LZ2), primary PCR was performed using pCBD(LZ1-LZ2) as a template and primers 17 and 18 (SEQ ID NOs. 24 and 25). Secondary PCR was performed using the PCR product as a template and primers 19 and 20 (SEQ ID NOs. 26 and 27), and pCBD(mLZ1(13/25/27)-LZ2)-inserted transformed strain was prepared in the same manner as above. The primers used in the present invention are shown in the following Table 3, wherein the substituted amino acids are underlined.

TABLE 3

| Primer name | Sequence (5'→3') | SEQ ID NO. |
|---|---|---|
| Primer 9 | GCAAGCGAGCAGCTGAAAAAGAAGTTACAAGCC | 16 |
| Primer 10 | GGCTTGTAACTTCTTTTTCAGCTGCTCGCTTGC | 17 |
| Primer 11 | CCAAGCATTGGAAAAAGAACTCGCGCAGATGGCC | 18 |
| Primer 12 | GGCCATCTGCGCGAGTTCTTTTTCCAATGCTTGG | 19 |
| Primer 13 | GGAAAAACCAAGCATTGAAAAAAAAACTCGCGCAG | 20 |
| Primer 14 | CTGCGCGAGTTTTTTTTTCAATGCTTGGTTTTTCC | 21 |
| Primer 15 | GAAGTTACAAGCCCTGAAGAAAAAACTTGCTCAGCTG | 22 |

TABLE 3 -continued

| Primer name | Sequence (5'→3') | SEQ ID NO. |
|---|---|---|
| Primer 16 | CAGCTGAGCAAGTTTTTCT<u>T</u>CAGGGCTTGTAACTTC | 23 |
| Primer 17 | CAAGCCCTGGAGAAA<u>G</u>AACTTGCTCAGCTGG | 24 |
| Primer 18 | CCAGCTGAGCAAGTT<u>C</u>TTTCTCCAGGGCTTG | 25 |
| Primer 19 | GGAAAAACCAAGCATTG<u>A</u>AAAA<u>G</u>AACTCGCGCAGATGGCC | 26 |
| Primer 20 | GGCCATCTGCGCGAGTT<u>C</u>TTTTT<u>C</u>AATGCTTGGTTTTTCC | 27 |

For protein expression, each gene was transformed into *E. coli* BL21(DE3) host cells, and protein expression was induced in the same manner as in Example 3.

Example 14

Figure 9:
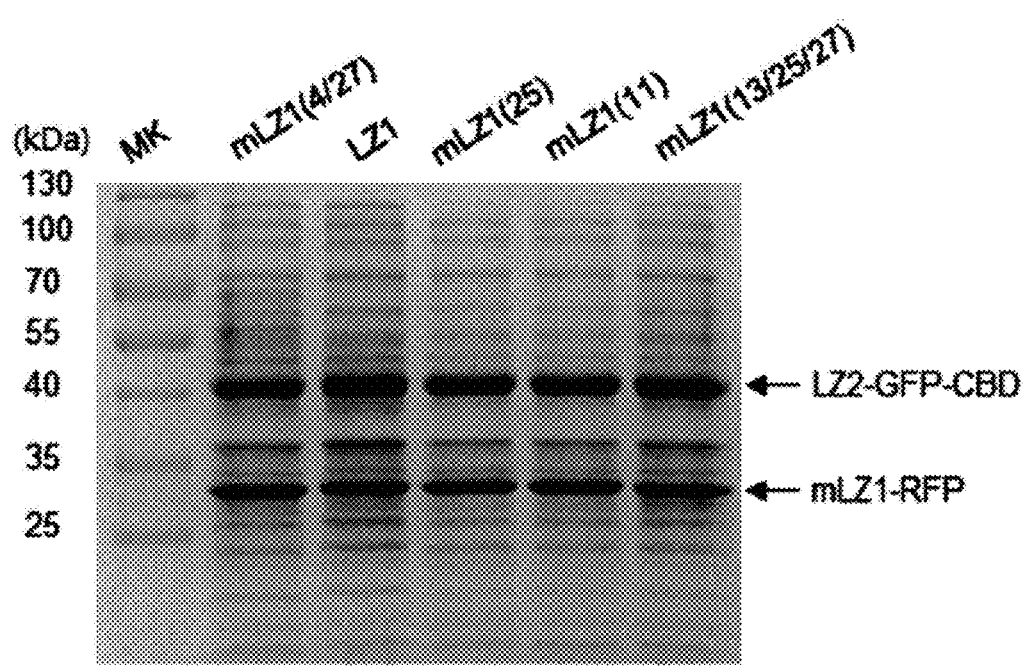
FIG. 9 is the results of SDS-PAGE for examination of intracellular expression levels of mLZ1-RFP and LZ2-GFP-CBD in mutant strains having different binding affinities of leucine zippers.

Quantitative Analysis of Interactions Between Leucine Zippers (LZs) Having Different Binding Affinities The results of expressing pCBD(LZ1-LZ2) or pCBD (mLZ1-LZ2) comprising LZ1 mutants (mLZ1(4/27), mLZ1 (25), mLZ1(11) or mLZ1(13/25/27)) in *E. coli* showed that mLZ1-RFP and LZ2-GFP-CBD were expressed in cells at a level of 1:1, and the expression levels were similar between the strains (FIG. 9). Co-localization of the GFP protein and the RFP protein in each strain was observed under a fluorescence microscope. As expected, as the binding affinity of the interaction was strong, co-localization of RFP in GFP inclusion bodies was observed. On the contrary, as the binding affinity was weaker, red fluorescent proteins were more dispersed in the cells (FIG. 10A). In addition, there was a remarkable difference in fluorescence intensity between GFPs and RFPs in inclusion bodies according to the binding affinity. As the binding affinity was increased, GFP intensity was increased whereas RFP intensity was decreased. On the contrary, as the binding affinity was decreased, GFP intensity was decreased whereas RFP intensity was increased (FIG. 10B). It was assumed that a reduction in RFP fluorescence according to the binding affinity was attributed to localization like the result of Example 8, and an increase in GFP fluorescence of inclusion bodies according to the binding affinity was consistent with the result of Example 10 showing fluorescence increased by interactions between leucine zippers, indicating that binding of LZ2-RFP influences activity of the GFP-inclusion bodies.

Figure 11:
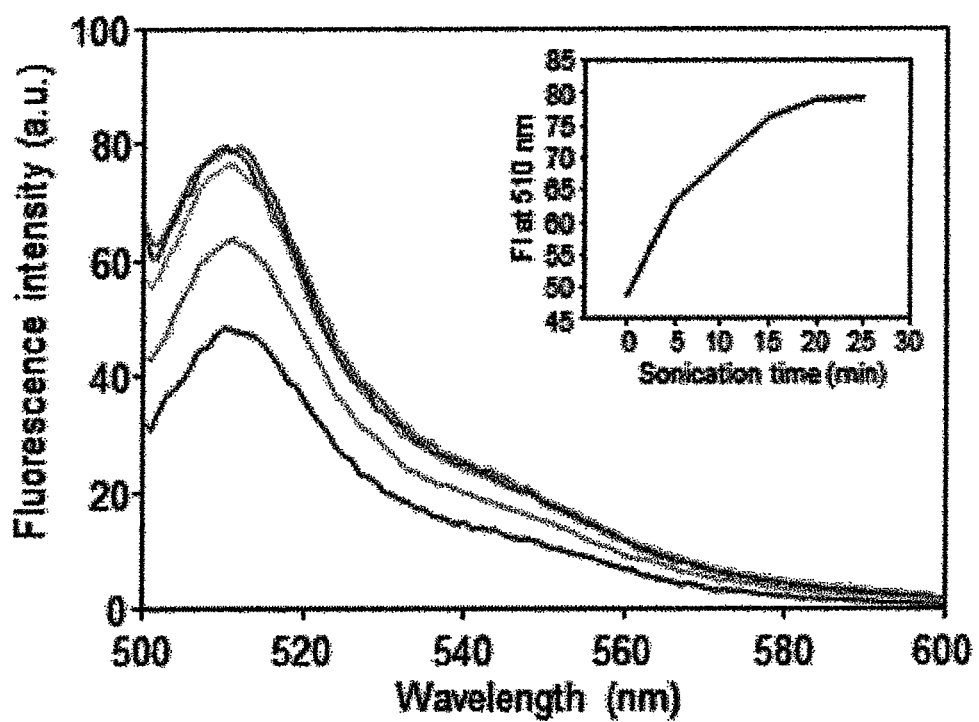
FIG. 11 shows that fluorescence was increased according to sonication time upon partial disruption of GFP inclusion bodies by sonication, in which GFP fluorescence is emitted at 510 nm.

The present inventors found that partial disruption of GFP inclusion bodies by sonication increased the entire fluorescence (FIG. 11), because inclusion bodies were swelled by physical impact to expose internal GFP fluorescence, implying that a large number of GFPs, which have not yet been activated appropriately, are still present inside the inclusion bodies. Meanwhile, in the present invention, the interaction of the leucine zippers occurs while the bait protein and the prey protein (LZ1-RFP, LZ2-GFP-CBD) are expressed and forms the inclusion bodies in cells, and thus the LZ2-RFPs may exist inside the inclusion bodies as well as outside the inclusion bodies. Thus, these results imply that RFPs present inside the inclusion bodies contributed to a recovery of the activity of the GFPs present inside the inclusion bodies by binding of leucine zippers.

Next, quantitative analysis of the same mutant strains were performed using flow cytometry. Like the results of fluorescence microscopy, as the binding affinity was increased, RFP intensity was decreased whereas GFP intensity was increased (FIG. 12A, C). In flow cytometry, a slight reduction of the RFP intensity was shown, but GFP intensity was greatly increased, which reflects a difference due to binding affinity (FIG. 12B). Contrary to expectations, the RFP intensity was slightly reduced according to the increased interactions, because the flow cytometer was equipped with a 488 nm argon laser. That is, EGFP has a high extinction coefficient ($\epsilon$) of 55,000 $M^{-1}$ $cm^{-1}$ at 488 nm, whereas RFP has a very low extinction coefficient ($\epsilon$) of 15,400 $M^{-1}$ $cm^{-1}$ at 488 nm which is a tenth of the maximum excitation (584 nm). That is, RFP has very low sensitivity, compared to EGFP. Moreover, GFP-RFP FRET inversely increases RFP fluorescence by interactions, resulting in the smaller reduction of the RFP fluorescence. However, two types of fluorescence were observed at the same time in flow cytometry, and thus interactions in *E. coli* can be more clearly detected by the increase and reduction of fluorescence according to binding affinity.

For quantitative analysis of flow cytometric data, a ratio of RFP to GFP fluorescence (FL2/FL1 ratio) was calculated. When the calculated values were compared with the reported affinity (affinity, 1/Kd), FCIB values were found to depend on affinity. In addition, an affinity of Kd=8~1000 uM could be detected by FICB method (FIG. 13). These results indicate that a broad range of affinities can be quantitatively measured and analyzed by FICB method.

Until now, it was very difficult to detect interactions in microorganisms by flow cytometry which has been considered as a sensitive and rapid method for the analysis of a large number of cells, because interactions in microorganisms are less dynamic than those in animal cells. However, by using the FCIB (fluorescence co-localization to inclusion bodies) method of the present invention, affinity of interactions could be quantitatively detected in a flow cytometer as well as in a fluorescence microscope. Therefore, it is expected that the present invention can be widely applied to analysis of interactions at a molecular level for high speed exploration of a large number of libraries (e.g., single chain antibody, decoy receptor, artificial scaffold protein) and improvement (specificity and affinity improvement).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

EFFECT OF THE INVENTION

The method of the present invention allows easy and rapid analysis of interactions between biomolecules in living cells, and allows rapid exploration and isolation of desired interacting proteins from a large number of libraries using a fluorescence microscope and a flow cytometer. Furthermore, the desired interacting proteins can be used to produce medicines that interrupt the interactions.

What is claimed is:

1. A method for detecting interaction between a bait protein and a prey protein in cells, comprising the steps of:
   (i) providing cells comprising a first construct and a second construct, wherein the first construct comprises a polynucleotide encoding a first fusion protein which comprises the bait protein, a first fluorescent protein and a CBD (cellulose-binding domain) protein, and wherein the second construct comprises a polynucleotide encoding a second fusion protein which comprises the prey protein and a second fluorescent protein;
   (ii) expressing the fusion proteins and allowing formation of inclusion bodies in the cells; and
   (iii) measuring fluorescence co-localization of the first and second fluorescent proteins in the inclusion bodies in the cells, wherein the fluorescence co-localization in the inclusion bodies of the cells indicates the interaction of the bait protein and the prey protein; and
   wherein the second fusion protein, when expressed in the absence of the first fusion protein, does not form inclusion bodies in the cells, and
   wherein the CBD protein facilitates formation of inclusion bodies.

2. The method according to claim 1, wherein the interaction between the bait protein and the prey protein is quantitatively detected.

3. The method according to claim 1, wherein the first and second constructs of step (i) exist within individual vectors or within a single vector.

4. The method according to claim 3, wherein the first and second constructs within the single vector are linked to each other by a nucleotide sequence including IRES (internal ribosome entry site).

5. The method according to claim 4, wherein the IRES has a nucleotide sequence of SEQ ID NO. 11.

6. The method according to claim 1, wherein the polynucleotides encoding the bait protein and the prey protein are those derived from libraries including genes encoding the proteins.

7. The method according to claim 1, wherein the first fluorescent protein and the second fluorescent protein emit different fluorescence colors.

8. The method according to claim 1, wherein the fluorescent protein is selected from the group consisting of GFP (Green Fluorescent Protein), EGFP (Enhanced Green Fluorescent Protein), mGFP (modified green fluorescent protein), RFP (Red Fluorescent Protein), mRFP (Monomeric Red Fluorescent Protein), ERFP (Enhanced Red Fluorescent Protein), DsRed (*Discosoma* sp. red fluorescent protein), BFP (Blue Fluorescent Protein), EBFP (Enhanced Blue Fluorescent Protein), CFP (Cyan Fluorescent Protein), CGFP (Cyan Green Fluorescent Protein), ECFP (Enhanced Cyan Fluorescent Protein), YFP (Yellow Fluorescent Protein), EYFP (Enhanced Yellow Fluorescent Protein), AzG (Azami Green), HcR (HcRed, *Heteractis crispa* red fluorescent protein), and BFP (Blue Fluorescent Protein).

9. The method according to claim 1, wherein the fluorescence detection is performed by florescence microscopy or flow cytometry.

10. The method according to claim 1, further comprising (iv) isolating the cell in which the prey protein interacts with the bait protein.

11. The method according to claim 10, wherein the polynucleotides encoding the bait protein and the prey protein are those derived from libraries including genes encoding the proteins.

12. The method according to claim 10, wherein the first fluorescent protein and the second fluorescent protein emit different fluorescence colors.

13. The method according to claim 10, wherein the fluorescent protein is selected from the group consisting of GFP (Green Fluorescent Protein), EGFP (Enhanced Green Fluorescent Protein), mGFP (modified green fluorescent protein), RFP (Red Fluorescent Protein), mRFP (Monomeric Red Fluorescent Protein), ERFP (Enhanced Red Fluorescent Protein), DsRed (*Discosoma* sp. red fluorescent protein), BFP (Blue Fluorescent Protein), EBFP (Enhanced Blue Fluorescent Protein), CFP (Cyan Fluorescent Protein), CGFP (Cyan Green Fluorescent Protein), ECFP (Enhanced Cyan Fluorescent Protein), YFP (Yellow Fluorescent Protein), EYFP (Enhanced Yellow Fluorescent Protein), AzG (Azami Green), HcR (HcRed, *Heteractis crispa* red fluorescent protein), and BFP (Blue Fluorescent Protein).

14. The method according to claim 10, wherein the isolation of the cell is performed by flow cytometry.

15. The method according to claim 10, further comprising (v) obtaining the prey protein which interacts with the bait protein from the isolated cell.

16. The method according to claim 10, wherein the first and second constructs of step (i) exist within individual vectors or with a single vector.

17. The method according to claim 16, wherein the first and second constructs within the single vector are linked to each other by a nucleic acid including IRES (internal ribosome entry site) sequence.

* * * * *

SEQUENCE LISTING

<160> NUMBER OF SEQ ID NOS: 29

<210> SEQ ID NO 1
<211> LENGTH: 30
<212> TYPE: PRT
<213> ORGANISM: Artificial Sequence
<220> FEATURE:
<223> OTHER INFORMATION: LZ1(Leucine zipper 1)

<400> SEQUENCE: 1

Glu Gln Leu Glu Lys Lys Leu Gln Ala Leu Glu Lys Lys Leu Ala Gln
1               5                   10                  15

Leu Glu Trp Lys Asn Gln Ala Leu Glu Lys Lys Leu Ala Gln
            20                  25                  30

<210> SEQ ID NO 2
<211> LENGTH: 29
<212> TYPE: PRT
<213> ORGANISM: Artificial Sequence
<220> FEATURE:
<223> OTHER INFORMATION: LZ2(Leucine zipper 2)

<400> SEQUENCE: 2

Ala Leu Lys Lys Glu Leu Gln Ala Asn Lys Lys Glu Leu Ala Gln Leu
1               5                   10                  15

Lys Trp Glu Leu Gln Ala Leu Lys Lys Glu Leu Ala Gln
            20                  25

<210> SEQ ID NO 3
<211> LENGTH: 27
<212> TYPE: DNA
<213> ORGANISM: Artificial Sequence
<220> FEATURE:
<223> OTHER INFORMATION: Primer 1

<400> SEQUENCE: 3
gatatacata tggtgagcaa gggcgag                                           27

<210> SEQ ID NO 4
<211> LENGTH: 34
<212> TYPE: DNA
<213> ORGANISM: Artificial Sequence
<220> FEATURE:
<223> OTHER INFORMATION: Primer 2

<400> SEQUENCE: 4
ggtgctcgag ttacttgtac agcttgtcca tgcc                                   34

<210> SEQ ID NO 5
<211> LENGTH: 65
<212> TYPE: DNA
<213> ORGANISM: Artificial Sequence
<220> FEATURE:
<223> OTHER INFORMATION: Primer 3

<400> SEQUENCE: 5
cctctagaaa taattttgtt taactttaag aaggagatat acatatggca agcgagcagc       60
tggaa                                                                   65

<210> SEQ ID NO 6
<211> LENGTH: 81
<212> TYPE: DNA
<213> ORGANISM: Artificial Sequence
<220> FEATURE:
<223> OTHER INFORMATION: Primer 4

-continued

<400> SEQUENCE: 6
caattctttt tgagggcca tatgataatc tccttcttaa agttaaacaa aattatttta    60
ggcgccggtg gagtggcggc c    81

<210> SEQ ID NO 7
<211> LENGTH: 81
<212> TYPE: DNA
<213> ORGANISM: Artificial Sequence
<220> FEATURE:
<223> OTHER INFORMATION: Primer 5

<400> SEQUENCE: 7
ggccgccact ccaccggcgc ctaaaataat tttgtttaac tttaagaagg agattatcat    60
atggccctca aaaagaatt g    81

<210> SEQ ID NO 8
<211> LENGTH: 42
<212> TYPE: DNA
<213> ORGANISM: Artificial Sequence
<220> FEATURE:
<223> OTHER INFORMATION: Primer 6

<400> SEQUENCE: 8
cagctcctcg cccttgctca cctgcgccag ttccttttc ag    42

<210> SEQ ID NO 9
<211> LENGTH: 42
<212> TYPE: DNA
<213> ORGANISM: Artificial Sequence
<220> FEATURE:
<223> OTHER INFORMATION: Primer 7

<400> SEQUENCE: 9
ctgaaaaagg aactggcgca ggtgagcaag ggcgaggagc tg    42

<210> SEQ ID NO 10
<211> LENGTH: 68
<212> TYPE: DNA
<213> ORGANISM: Artificial Sequence
<220> FEATURE:
<223> OTHER INFORMATION: Primer 8

<400> SEQUENCE: 10
gcagccaact cagcttcctt tcgggctttg ttagcagccg gatctcagcc gaccgtgcag    60
ggcgtgcc    68

<210> SEQ ID NO 11
<211> LENGTH: 36
<212> TYPE: DNA
<213> ORGANISM: Artificial Sequence
<220> FEATURE:
<223> OTHER INFORMATION: IRES

<400> SEQUENCE: 11
aataattttg tttaactta agaaggagat tatcat    36

<210> SEQ ID NO 12
<211> LENGTH: 30
<212> TYPE: PRT
<213> ORGANISM: Artificial Sequence
<220> FEATURE:
<223> OTHER INFORMATION: mLZ1(4/27)

<400> SEQUENCE: 12

Glu Gln Leu Lys Lys Lys Leu Gln Ala Leu Glu Lys Lys Leu Ala Gln
1               5                   10                  15

Leu Glu Trp Lys Asn Gln Ala Leu Glu Lys Glu Leu Ala Gln
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: mLZ1(25)

<400> SEQUENCE: 13

Glu Gln Leu Glu Lys Lys Leu Gln Ala Leu Glu Lys Lys Leu Ala Gln
1               5                   10                  15

Leu Glu Trp Lys Asn Gln Ala Leu Lys Lys Lys Leu Ala Gln
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: mLZ1(11)

<400> SEQUENCE: 14

Glu Gln Leu Glu Lys Lys Leu Gln Ala Leu Lys Lys Lys Leu Ala Gln
1               5                   10                  15

Leu Glu Trp Lys Asn Gln Ala Leu Glu Lys Lys Leu Ala Gln
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: mLZ1(13/25/27)

<400> SEQUENCE: 15

Glu Gln Leu Glu Lys Lys Leu Gln Ala Leu Glu Lys Glu Leu Ala Gln
1               5                   10                  15

Leu Glu Trp Lys Asn Gln Ala Leu Lys Lys Glu Leu Ala Gln
            20                  25                  30

<210> SEQ ID NO 16
<211> LENGTH: 33
<212> TYPE: DNA
<213> ORGANISM: Artificial Sequence
<220> FEATURE:
<223> OTHER INFORMATION: Primer 9

<400> SEQUENCE: 16
gcaagcgagc agctgaaaaa gaagttacaa gcc                                    33

<210> SEQ ID NO 17
<211> LENGTH: 33
<212> TYPE: DNA
<213> ORGANISM: Artificial Sequence
<220> FEATURE:
<223> OTHER INFORMATION: Primer 10

<400> SEQUENCE: 17
ggcttgtaac ttcttttca gctgctcgct tgc                                     33

-continued

```
<210> SEQ ID NO 18
<211> LENGTH: 34
<212> TYPE: DNA
<213> ORGANISM: Artificial Sequence
<220> FEATURE:
<223> OTHER INFORMATION: Primer 11

<400> SEQUENCE: 18
ccaagcattg gaaaaagaac tcgcgcagat ggcc                              34

<210> SEQ ID NO 19
<211> LENGTH: 34
<212> TYPE: DNA
<213> ORGANISM: Artificial Sequence
<220> FEATURE:
<223> OTHER INFORMATION: Primer 12

<400> SEQUENCE: 19
ggccatctgc gcgagttctt tttccaatgc ttgg                              34

<210> SEQ ID NO 20
<211> LENGTH: 35
<212> TYPE: DNA
<213> ORGANISM: Artificial Sequence
<220> FEATURE:
<223> OTHER INFORMATION: Primer 13

<400> SEQUENCE: 20
ggaaaaacca agcattgaaa aaaaactcg cgcag                              35

<210> SEQ ID NO 21
<211> LENGTH: 35
<212> TYPE: DNA
<213> ORGANISM: Artificial Sequence
<220> FEATURE:
<223> OTHER INFORMATION: Primer 14

<400> SEQUENCE: 21
ctgcgcgagt tttttttca atgcttggtt tttcc                              35

<210> SEQ ID NO 22
<211> LENGTH: 37
<212> TYPE: DNA
<213> ORGANISM: Artificial Sequence
<220> FEATURE:
<223> OTHER INFORMATION: Primer 15

<400> SEQUENCE: 22
gaagttacaa gccctgaaga aaaaacttgc tcagctg                           37

<210> SEQ ID NO 23
<211> LENGTH: 37
<212> TYPE: DNA
<213> ORGANISM: Artificial Sequence
<220> FEATURE:
<223> OTHER INFORMATION: Primer 16

<400> SEQUENCE: 23
cagctgagca agttttttct tcagggcttg taacttc                           37

<210> SEQ ID NO 24
<211> LENGTH: 31
<212> TYPE: DNA
<213> ORGANISM: Artificial Sequence
<220> FEATURE:
<223> OTHER INFORMATION: Primer 17
```

```
<400> SEQUENCE: 24
caagccctgg agaaagaact tgctcagctg g                                    31

<210> SEQ ID NO 25
<211> LENGTH: 31
<212> TYPE: DNA
<213> ORGANISM: Artificial Sequence
<220> FEATURE:
<223> OTHER INFORMATION: Primer 18

<400> SEQUENCE: 25
ccagctgagc aagttctttc tccagggctt g                                    31

<210> SEQ ID NO 26
<211> LENGTH: 41
<212> TYPE: DNA
<213> ORGANISM: Artificial Sequence
<220> FEATURE:
<223> OTHER INFORMATION: Primer 19

<400> SEQUENCE: 26
ggaaaaacca agcattgaaa aagaactcg cgcagatggc c                          41

<210> SEQ ID NO 27
<211> LENGTH: 41
<212> TYPE: DNA
<213> ORGANISM: Artificial Sequence
<220> FEATURE:
<223> OTHER INFORMATION: Primer 20

<400> SEQUENCE: 27
ggccatctgc gcgagttctt ttttcaatgc ttggtttttc c                         41

<210> SEQ ID NO 28
<211> LENGTH: 108
<212> TYPE: PRT
<213> ORGANISM: Artificial Sequence
<220> FEATURE:
<223> OTHER INFORMATION: CBD(cellulose binding domain)

<400> SEQUENCE: 28

Ser Gly Pro Ala Gly Cys Gln Val Leu Trp Gly Val Asn Gln Trp Asn
1               5                   10                  15

Thr Gly Phe Thr Ala Asn Val Thr Val Lys Asn Thr Ser Ser Ala Pro
            20                  25                  30

Val Asp Gly Trp Thr Leu Thr Phe Ser Phe Pro Ser Gly Gln Gln Val
        35                  40                  45

Thr Gln Ala Trp Ser Ser Thr Val Thr Gln Ser Gly Ser Ala Val Thr
    50                  55                  60

Val Arg Asn Ala Pro Trp Asn Gly Ser Ile Pro Ala Gly Gly Thr Ala
65                  70                  75                  80

Gln Phe Gly Phe Asn Gly Ser His Thr Gly Thr Asn Ala Ala Pro Thr
                85                  90                  95

Ala Phe Ser Leu Asn Gly Thr Pro Cys Thr Val Gly
            100                 105

<210> SEQ ID NO 29
<211> LENGTH: 327
<212> TYPE: DNA
<213> ORGANISM: Artificial Sequence
<220> FEATURE:
<223> OTHER INFORMATION: CBD(cellulose binding domain)
```

-continued

```
<400> SEQUENCE: 29
agtggtccgg ccgggtgcca ggtgctgtgg ggcgtcaacc agtggaacac cggcttcacc      60
gcgaacgtca ccgtgaagaa cacgtcctcc gctccggtcg acggctggac gctcacgttc     120
agcttcccgt ccggccagca ggtcacccag gcgtggagct cgacggtcac gcagtccggc     180
tcggccgtga cggtccgcaa cgccccgtgg aacggctcga tcccggcggg cggcaccgcg     240
cagttcggct tcaacggctc gcacacgggc accaacgccg cgccgacggc gttctcgctc     300
aacggcacgc cctgcacggt cggctga                                        327
```